(12) United States Patent
Vogt et al.

(10) Patent No.: US 10,463,413 B2
(45) Date of Patent: Nov. 5, 2019

(54) STORAGE AND MIXING SYSTEM FOR PASTY CEMENT COMPONENTS AND METHOD THEREFOR

(71) Applicant: Heraeus Medical GmbH, Wehrheim (DE)

(72) Inventors: Sebastian Vogt, Erfurt (DE); Thomas Kluge, Vallendar (DE)

(73) Assignee: HERAEUS MEDICAL GMBH, Wehrheim (DE)

( * ) Notice: Subject to any disclaimer, the term of this patent is extended or adjusted under 35 U.S.C. 154(b) by 314 days.

(21) Appl. No.: 15/460,530

(22) Filed: Mar. 16, 2017

(65) Prior Publication Data
US 2017/0265922 A1 Sep. 21, 2017

(30) Foreign Application Priority Data
Mar. 17, 2016 (DE) .................. 10 2016 104 950

(51) Int. Cl.
*A61B 17/58* (2006.01)
*A61B 17/60* (2006.01)
(Continued)

(52) U.S. Cl.
CPC ...... *A61B 17/8833* (2013.01); *A61B 17/8822* (2013.01); *A61B 17/8825* (2013.01);
(Continued)

(58) Field of Classification Search
CPC combination set(s) only.
See application file for complete search history.

(56) References Cited

U.S. PATENT DOCUMENTS

| | | | |
|---|---|---|---|
| 2,446,501 | A | 8/1948 | Weber |
| 3,188,056 | A | 6/1965 | Trumbull et al. |

(Continued)

FOREIGN PATENT DOCUMENTS

| | | | |
|---|---|---|---|
| CN | 1835873 | A | 9/2006 |
| CN | 101160247 | A | 4/2008 |

(Continued)

OTHER PUBLICATIONS

Kuehn, Klaus-Dieter; "Knochenzemente fuer die Endoprothetik"; Springer-Verlag, 2000, pp. 18-19, Springer-Verlag of BertelmannSpringer publishing group, Berlin, Germany.

(Continued)

*Primary Examiner* — Sameh R Boles
(74) *Attorney, Agent, or Firm* — Norris McLaughlin, P.A.

(57) ABSTRACT

Storage and mixing systems for pasty two-component polymethyl methacrylate bone cements comprise a tubular cartridge having a cylindrical inner chamber, a cartridge head, which closes one end of the tubular cartridge at the front side, a partition that is disposed axially in the cylindrical inner chamber of the cartridge. The partition divides the cylindrical inner chamber of the cartridge bounded by the cartridge head into two cavities that are spatially separated from one another, wherein a first pasty cement component is present in the first cavity and a second pasty cement component is present in the separate second cavity. The systems further comprising two dispensing plungers axially displaceable in the two cavities of the cartridge, wherein the dispensing plungers close the two cavities on the back side of the cavities situated opposite the cartridge head, a bending device for deforming the partition, wherein the bending device is axially movable in the cartridge and is disposed, or is to be disposed, behind the dispensing plungers, as seen from the cartridge head, wherein the bending (Continued)

device has a deflection surface that is inclined with respect to the axis of the cartridge and pushes the partition laterally in the direction of the inside wall of the cartridge when the bending device is pushed into the cartridge.

24 Claims, 13 Drawing Sheets

(51) Int. Cl.
    *A61F 2/00*     (2006.01)
    *A61B 17/88*     (2006.01)
    *B01F 3/10*     (2006.01)
    *B01F 15/02*     (2006.01)
    *C08F 120/18*     (2006.01)
    *A61L 27/16*     (2006.01)
    *B05C 17/005*     (2006.01)
    *B01F 5/06*     (2006.01)
    *B01F 13/00*     (2006.01)
    *B05C 17/01*     (2006.01)

(52) U.S. Cl.
    CPC ............... *A61L 27/16* (2013.01); *B01F 3/10* (2013.01); *B01F 5/0615* (2013.01); *B01F 13/0023* (2013.01); *B01F 15/0237* (2013.01); *B05C 17/00553* (2013.01); *B05C 17/00576* (2013.01); *B05C 17/00583* (2013.01); *C08F 120/18* (2013.01); *A61B 2017/8838* (2013.01); *A61L 2400/06* (2013.01); *A61L 2430/02* (2013.01); *B05C 17/00509* (2013.01); *B05C 17/00513* (2013.01); *B05C 17/00596* (2013.01); *B05C 17/0106* (2013.01)

(56) References Cited

U.S. PATENT DOCUMENTS

| | | | |
|---|---|---|---|
| 4,493,436 A * | 1/1985 | Brokaw | B05C 17/00553 222/137 |
| 6,769,564 B2 | 8/2004 | Prestele | |
| 6,935,541 B1 | 8/2005 | Campbell et al. | |
| 8,544,683 B2 | 10/2013 | Springhorn et al. | |
| 9,095,871 B2 | 8/2015 | Vogt et al. | |
| 2001/0004082 A1 | 6/2001 | Keller et al. | |
| 2002/0153377 A1 | 10/2002 | Prestele | |
| 2004/0074927 A1 | 4/2004 | Lafond | |
| 2004/0129122 A1 | 7/2004 | Brugner et al. | |
| 2006/0274601 A1 | 12/2006 | Seaton, Jr. | |
| 2008/0195082 A1 | 8/2008 | Pauser et al. | |
| 2009/0105144 A1 | 4/2009 | Vogt et al. | |
| 2009/0105366 A1 | 4/2009 | Vogt et al. | |
| 2009/0266843 A1 | 10/2009 | Griesbaum et al. | |
| 2011/0272436 A1 | 11/2011 | Vogt et al. | |

FOREIGN PATENT DOCUMENTS

| | | |
|---|---|---|
| DE | 25 21 392 | 11/1976 |
| DE | 201 06 406 U1 | 8/2002 |
| DE | 202005010206 U1 | 9/2005 |
| DE | 10 2005 017 599 A1 | 10/2006 |
| DE | 20 2006014087 U1 | 1/2007 |
| DE | 102007052116 A1 | 4/2009 |
| DE | 102007050762 B3 | 5/2009 |
| DE | 102008030312 A1 | 1/2010 |
| DE | 20 2014 102 416 U1 | 7/2014 |
| DE | 10 2013 107 955 A1 | 1/2015 |
| EP | 0 119 847 A2 | 9/1984 |
| EP | 1392450 B1 | 7/2005 |
| FR | 14 68 507 A | 2/1967 |
| JP | S59-187569 A | 10/1984 |
| JP | 2011-235961 A | 11/2011 |
| WO | 2011/016645 A2 | 2/2011 |

OTHER PUBLICATIONS

Canadian Office Action dated Apr. 13, 2018 for corresponding application No. 2690241.

English translation of Chinese Office Action corresponding to Chinese application No. 201710161692.1, dated Sep. 14, 2018.

* cited by examiner ic
STORAGE AND MIXING SYSTEM FOR PASTY CEMENT COMPONENTS AND METHOD THEREFOR This application claims foreign priority benefit under 35 U.S.C. 119 of German Application No. DE 10 2016 104 950.6 filed Mar. 17, 2016.

DESCRIPTION OF THE DISCLOSURE

The invention relates to a storage and mixing system for pasty two-component polymethyl methacrylate bone cements, the storage and mixing system comprising a tubular cartridge having a cylindrical inner chamber.

The invention also relates to a method for mixing pasty cement components of a cement dough, and in particular of a pasty polymethyl methacrylate bone cement, using such a storage and mixing system.

The subject matter of the invention is thus a simple storage and mixing system for pasty two-component polymethyl methacrylate bone cements, which is cost-effective to produce and can be used to mix and dispense the highly viscous, pasty cement components of the polymethyl methacrylate bone cement using manually operable dispensing devices.

Conventional polymethyl methacrylate bone cements (PMMA bone cements) are composed of a powder component and a liquid monomer component (K.-D. Kühn: Knochenzemente für die Endoprothetik: Ein aktueller Vergleich der physikalischen and chemischen Eigenschaften handelsüblicher PMMA-Zemente (Bone Cements for Endoprostheses: A Current Comparison of the Physical and Chemical Properties of Commercially Available PMMA Cements). Springer-Verlag Berlin Heidelberg New York, 2001). After the cement powder has been mixed with the liquid monomer component, these polymethyl methacrylate bone cements are applied while still in an uncured, pasty state in the form of a cement dough. When mixing systems are used, the cement dough is present in a cartridge in the case of powder/liquid cements. The cement dough is pushed out of this cartridge by the movement of a dispensing plunger. The dispensing plungers usually have a diameter between 30 mm and 40 mm and thus have a surface area of 7.0 $cm^2$ to 12.5 $cm^2$ on the outer side on which the pusher of the dispensing device engages during the process of pressing out. The movement of the dispensing plunger is effectuated by manually operable mechanical dispensing devices, which are also referred to as applicators. These dispensing devices or applicators normally have a pressing force in the range of approximately 1.5 kN to 3.5 kN.

Pasty two-component bone cements, as they are known from DE 10 2007 050 762 B3, DE 10 2008 030 312 A1 and DE 10 2007 052 116 B4, for example, constitute a more recent development. In the case of these two-component bone cements, two pasty cement components are stored in two separate cartridges comprising two separate dispensing plungers. During the application, the two pastes are pressed out of the cartridges and into a static mixer by the movement of the dispensing plunger, and are dispensed through a dispensing tube after having been mixed. A suitable composition of the pasty cement components immediately yields a cement dough that is dry to the touch and ready to be applied after the two cement components have been mixed. This eliminates waiting periods until the non-tacky state of the cement dough is reached, which necessarily occur with existing conventional polymethyl methacrylate bone cements all the time. As a result, valuable time is saved in the operating room.

Experiments conducted by the inventors within the scope of the present invention showed that the drop-in pressure at the static mixer in the dispensing tube is very high during the pressing process of the cartridges due to the high viscosity of the pasty cement components. Experiments conducted by the inventors also showed that a pressing force of greater than 7 kN is needed when using a conical dispensing tube having an overall length of approximately 17 cm and an inside diameter of 11 mm at the cartridge head, and when using ten static mixing elements, in order to press out the highly viscous cement pastes at a dispensing rate acceptable for the medical user.

When existing, conventional PMMA bone cements, which are composed of a liquid monomer component and a cement powder component stored separately therefrom, are applied, the created cement dough is pressed out with the aid of manually operable dispensing devices after the two cement components have been mixed in cementing systems or vacuum cementing systems. These simple mechanical dispensing devices use in particular clamping rods for pressing, which are driven by a manually actuatable rocker lever. The manually driven dispensing devices have been tried and tested around the globe for decades and so far represent the prior art. The advantage of these dispensing devices is that the medical user, by way of the manual force to be applied, has a feel for the penetration resistance of the bone cement dough in the bone structures (spongiosa).

When highly viscous pasty cement components are used with cartridges, in which the dispensing plungers on the outer plunger sides on which the pushers of the dispensing devices engage have a total surface area in the range of 7.0 $cm^2$ to 12.5 $cm^2$, these devices cannot be operated manually or only with very high force expenditure. This high force expenditure cannot be expected of medical users in the operating room.

Electrically driven pressing devices are also known from the adhesives and sealants field. These devices can be driven either by rechargeable batteries and batteries, or with the aid of a stationary power supply unit. These devices, some of which have very high pressing forces, are able to press out particularly viscous, pasty compounds. The disadvantage of using electric motors, however, is that these contain non-ferrous metals and are expensive to procure. Such devices require complex sterilization, or even replacement, in the operating area, which must be kept in a sterile condition. If electrical wiring is present, the movement of the user in the operating room may be impeded.

Moreover, pneumatic devices have been proposed. These devices require a stationary or mobile compressed air connection (U.S. Pat. No. 2,446,501 A; DE 20 2005 010 206 U1). This necessitates air hoses, which can impede the movement of the user.

As an alternative, it is also possible to use compressed gas cartridges to provide compressed gas. For this purpose, devices have been proposed in which the compressed gas supply is controlled by a valve, and additionally the flow of the viscous compound is controlled by a second valve (US 2004/0074927 A1; U.S. Pat. No. 6,935,541 B1). In these devices, the gas cartridges are integrated in the devices. Such systems connected to compressed air or compressed gas cartridges always necessitate a compressed gas source, without which the systems cannot be used.

U.S. Pat. No. 8,544,683 B2 discloses a cartridge system, which is suitable for admixing a small amount to a primary component. In addition to a cartridge, a second smaller cartridge is disposed on the cartridge system, wherein an advancement of a dispensing plunger in the larger cartridge also drives a dispensing plunger in the smaller cartridge by way of a shared connecting element. However, the system is not suitable for mixing the viscous pasty cement components of PMMA bone cement.

A coaxial cartridge system comprising a special plunger system is described in the patent EP 1 392 450 B1. The cartridge system is used in the materials chemistry field for storing and mixing pasty two-component sealing compounds. The plunger system disclosed therein has a cylindrical dispensing plunger for the central cartridge, and an annular dispensing plunger for the second, coaxially disposed cartridge. Both dispensing plungers are driven behind the sealing surfaces by a support element, which on the back side includes multiple abutment surfaces for the pushers of the dispensing device. The support element includes curved blades. During axial action of the pusher of a press-out device, the two plungers are moved forward in the direction of the cartridge head. In this process, the pasty components present in the coaxial cartridges are pushed in the direction of the cartridge head. At the same time, two blades divide the wall of the inner coaxial cartridge into two parts. The disadvantage of this system is that two cutting processes necessarily take place simultaneously. This means that energy is required for both cutting processes, which is therefore not available for the actual advancement of the two pasty components. Due to the static mixers disposed in the dispensing tube and the high viscosity of the cement components, the mixing of pasty cement components for PMMA bone cements requires a large amount of advancement energy, which in the case of larger cartridges can no longer be applied manually, hazard-free and by using conventional dispensing devices. A loss of advancement energy as a result of two simultaneously occurring cutting processes can thus pose a problem, in particular in the case of high-viscosity pasty components. Moreover, coaxial cartridges cannot be readily filled with cement components of a PMMA bone cement. In particular, when only small amounts of the PMMA bone cement are to be present, the free cross-sections of the outer coaxial cartridge become so small that these can no longer be filled by way of conventional methods.

Thus, it is the object of the invention to overcome the drawbacks of the prior art. In particular, a simple storage and mixing system for pasty two-component polymethyl methacrylate bone cements which is inexpensive to produce, and a method for producing a bone cement using a storage and mixing system, are to be provided, wherein it is to be possible to render the storage and mixing system operational as a single-use, ready-to-use system in the simplest manner within just a few seconds, requiring a minimal number of assembly steps, and the system, after being connected to manually drivable medical dispensing devices or applicators, generating a homogeneously mixed cement dough immediately after the manual actuation of the dispensing device has begun, and dispensing this at the dispensing opening of a dispensing tube. The manually operable dispensing devices used previously in operating rooms for conventional polymethyl methacrylate bone cements, which each comprise a push rod and possibly a plate, are to be usable to dispense the two-component polymethyl methacrylate bone cement, or the cement dough, using the storage and mixing system to be developed. This is intended to avoid the procurement of special dispensing devices for dispensing pasty two-component polymethyl methacrylate bone cements.

The storage and mixing system to be developed should preferably not necessitate two push rods or pushers that are connected to one another and that are to be advanced synchronously, so that the entire device is not significantly longer and larger than the mixing systems, and vacuum mixing systems, previously customary for conventional powder/liquid polymethyl methacrylate bone cements. A simple solution is to be found, which allows two pasty cement components to be driven from the device synchronously and manually, preferably by way of only one push rod or only one pusher and possibly a plate attached thereto. It is to be possible to store the pasty cement components of the bone cement separately from one another reliably within the storage and mixing system. For use, it should be possible to reliably combine the two pasty cement components. The storage and mixing system is also to be able to dispense a small volume of the homogeneously mixed cement dough of approximately 50 ml, and of no more than 70 ml, without leaving larger residual amounts (more than 15 ml) behind in the system and requiring complex disposal. Larger volumes of the cement dough are not sought. The described small amounts are sufficient for many applications, such as surgeries in the knee area.

The transition from the cartridge to the dispensing tube is preferably to be designed such that the flow resistance of the pasty cement components is as low as possible when these are pressed out. The cement components used must be pasty cement components that can be applied directly after being pressed out, which is to say which require no time for swelling of the PMMA bone cement. The device is to be configured such that the design, to as great an extent as possible, precludes the user from confusing the relevant assembly steps, and that the storage and mixing system can also be employed by substantially untrained staff. Furthermore, a method for mixing the pasty cement components and for dispensing the homogeneously mixed cement dough is to be provided.

The objects of the invention are achieved by a storage and mixing system for pasty two-component polymethyl methacrylate bone cements, the storage and mixing system comprising:

a tubular cartridge having a cylindrical inner chamber;

a cartridge head, which closes one end of the tubular cartridge at the front side;

a partition that is disposed axially in the cylindrical inner chamber of the cartridge, wherein the partition divides the cylindrical inner chamber of the cartridge bounded by the cartridge head into two cavities that are spatially separated from one another, wherein a first pasty cement component is present in the first cavity and a second pasty cement component is present in the separate second cavity;

two dispensing plungers disposed axially displaceably in the two cavities of the cartridge, wherein the dispensing plungers close the two cavities on the back side of the cavities situated opposite the cartridge head;

a bending device for deforming the partition, wherein the bending device is axially movable in the cartridge and is disposed, or is to be disposed behind of the dispensing plungers, as seen from the cartridge head, wherein the bending device comprises a deflection surface that is inclined with respect to the axis of the cartridge and pushes the partition laterally in the direction of the inside wall of the cartridge when the bending device is pushed into the cartridge.

The bending device is pushed into the cartridge from the back side.

It is preferred according to the invention if the partition is not rigidly connected to the cartridge and/or if the partition is disposed as a separate part in the cartridge. This allows the partition to be detached from the inside wall of the cartridge more easily and with greater control, and less energy is needed to advance the bending device, since the partition does not have to be mechanically separated from the inside wall of the cartridge.

In storage and mixing systems according to the invention, it may be provided that a rear end of the partition, which is disposed behind the dispensing plungers, as seen from the cartridge head, is to be fastened or is fastened to the cartridge so that the rear end of the partition does not detach from the cartridge when the bending device moves into the cartridge.

The fastening can take place by way of a hook or a pin on the cartridge, and in particular by way of a pin having a mushroom head on the cartridge, which can be inserted or is inserted into a hole provided in the partition. The rear end of the partition, however, can also be adhesively attached, or theoretically can even be designed in one piece with the cartridge and joined thereto.

In this way, it is achieved that the partition does not collapse in front of the dispensing plungers, which is to say between the dispensing plungers and the cartridge head, when the bending device and the dispensing plungers are being advanced, whereby the movement of the dispensing plungers into the cavities is impaired by the buckling of the partition.

It may be provided that a fastening element is disposed at the rear end of the partition, wherein the fastening element is to be fastened to a mating fastening element in the region of the rear side of the cartridge, wherein preferably a hole is provided in the partition as the fastening element, and a hook or a pin is provided as the mating fastening element.

In this way, fastening means and mating fastening means that can be implemented particularly easily and cost-effectively can be provided.

According to a preferred refinement of the present invention, it may be provided that a passage is provided in the bending device, or that the bending device forms a passage together with the inside wall of the cartridge, wherein the deflection surface is provided in the passage, and the partition is to be fed through the passage or is fed through the passage, wherein the partition moves through the passage when the bending device is moving into the cartridge.

This allows stable and reproducible deflection and deformation of the partition by way of guidance of the partition in the passage of the bending device. In the passage, the partition is preferably deflected in the region of the deflection surface perpendicularly to the surface area of the partition and/or is bent about an axis parallel to the axis of the cartridge.

It may preferably also be provided that a rear portion of the partition, which starts behind the front side of the dispensing plungers, is shaped in the manner of a strip, which is not connected to the inside wall of the cartridge. This strip can particularly preferably be fed through the bending device. The front side of the dispensing plungers is the side of the dispensing plungers that faces the cartridge head or the dispensing tube and bounds the two cavities containing the cement components therein.

According to the invention, it may be provided that the partition is connected to the inside wall of the cartridge via a predetermined breaking point, or that the partition is detachably connected to the inside wall of the cartridge. In this way, the partition can be easily removed from the inside wall of the cartridge. The partition is not designed as one piece with the cartridge if it is detachably connected to the inside wall of the cartridge. The partition is not cut by the bending device when being deformed by the bending device. Thus, previously contiguous material is not severed during the deformation if the partition is detachable from the inside wall of the cartridge.

Preferably, it may be provided that the partition is connected to the inside wall of the cartridge via a predetermined breaking point, or that the partition is detachably connected to the inside wall of the cartridge, so that the partition detaches from the inside wall of the cartridge when the partition is being deformed by the movement of the bending device into the cartridge.

In this way, it is achieved that the partition can be detached from the inner side of the cartridge without great effort, but that, at the same time, sufficient sealing of the two cavities is present beforehand, whereby the cement components can be stored in the cavities.

It may be provided that the partition is detachably connected at both lateral edges to a respective guide element in or on the inside wall of the cartridge, and preferably is inserted into a respective groove in the inside wall of the cartridge, wherein the guide element and the lateral edges of the partition are sealed in a fluid-tight manner with one another.

The partition can thus be detached from the inside wall of the cartridge without breaking open a predetermined breaking point. At the same time, the necessary tightness between the two cavities can be achieved beforehand by way of the guide element or the groove and the inserted partition, so that the two cement components do not prematurely react with one another.

The partition preferably engages in the two guide elements in a form-locked manner.

It may be provided that a seal is present in the groove, or on the edge of the partition inserted into the groove, by way of which the two cavities are sealed with respect to one another.

Furthermore, it may be provided that that the dispensing plungers are connected or connectable to one another at the back side situated opposite the cartridge head via the bending device, and preferably that the dispensing plungers are disposed at a distance from one another by way of the bending device such that the gap present between the dispensing plungers is smaller than or equal to the thickness of the partition.

It is thus ensured that the dispensing plungers run in the cavities in a stable manner, do not tilt, and are tightly sealed with respect to the partition, so that the cement components cannot flow backward out of the cartridge and thereby contaminate the surrounding area. By limiting the gap with respect to the thickness of the partition, it is achieved that the dispensing plungers run in the cavities in a stable manner, and the partition can be guided and deformed well by the bending device.

According to the invention, it may be provided that the partition is seated against the lateral surface of the cylindrical inner chamber of the cartridge along two connecting lines which bound the lateral surface, wherein the connecting lines are preferably disposed opposite one another, and particularly preferably the axis of the cartridge is situated in the partition. If the two grooves are present, these extend along these connecting lines. The connecting lines preferably run axially with respect to the cartridge.

In this way, the dispensing plungers can be evenly advanced in the cavities, and the partition can be traversed or deformed evenly by the bending device using an even force.

According to a preferred embodiment of the present invention, it may be provided that the cavities have a semi-circular or circular segment-shaped cross-section, and the dispensing plungers have a matching cross-section, whereby the dispensing plungers close off the cavities in every axial position in the cavities.

In this way, a storage and mixing system is made possible that is particularly simple and cost-effective to implement.

Furthermore, it may be provided that the partition has a thickness of no more than 1.5 mm, and preferably of no more than 1.0 mm, and/or that the partition has such a thickness that the partition can be deformed by the bending device, onto which an advancing force of 1 kN acts, and pushed in the direction of the inside wall of the cartridge.

It is thus ensured that the partition, when made of conventional plastic materials, can be deformed without difficulty by manually driven dispensing devices acting on the bending device and can be pushed in the direction of the inside wall of the cartridge, while the cement components are being pressed out of the cavities by the dispensing plungers.

Preferred storage and mixing can be characterized in that the storage and mixing system comprises a dispensing tube, on which a fastening means for fastening the dispensing tube to the cartridge is provided, wherein the dispensing tube instead of the cartridge head is preferably to be fastened to the cartridge.

The fastening means is preferably an internal thread, which can be screwed onto an external thread on the cartridge. The external thread on the cartridge is particularly preferably also used to detachably fasten the cartridge head to the cartridge.

According to the invention, a static mixer is preferably disposed in the dispensing tube. The invention also proposes that a static mixer be disposed in the dispensing tube, and that an internal thread, an external thread, elements of a bayonet catch and/or detent elements of a detent closure be attached to the base of the dispensing tube as connecting means.

In this way, the dispensing tube can be used to mix the cement components and apply these with pinpoint precision. A longer dispensing tube is advantageous especially for applying a PMMA bone cement to sites that are difficult to access.

All generally known static mixers may be used as the static mixer. An internal thread and/or an external thread and/or elements of a bayonet catch and/or detent elements of a detent closure are attached to the base of the dispensing tube as connecting means. These connecting means can be used to connect the dispensing tube to the cartridge in a mechanically stable manner. This connection must be stable, so that the high pressure that occurs when the pasty cement components are pressed out does not cause the dispensing tube to become detached from the cartridge. Threads are thus particularly advantageous connecting means, and double threads are especially particularly advantageous.

In the case of storage and mixing systems comprising a dispensing tube, it may furthermore be provided that the ratio of the diameter of the inner chamber of the cartridge to the inside diameter of the dispensing tube is smaller than 5 to 2, wherein the ratio of the diameter of the inner chamber of the cartridge to the inside diameter of the dispensing tube is preferably smaller than or equal to 2 to 1, and especially particularly preferably the ratio of the diameter of the inner chamber of the cartridge to the inside diameter of the dispensing tube is 8 to 5.

In this way, it is achieved that a sufficient flow velocity of the PMMA bone cement is achieved at the dispensing opening of the dispensing tube during the advancement of the dispensing plungers.

In particular, it may also be in particular for provided that the diameter of the inner chamber of the cartridge is smaller than or equal to 25 mm, wherein the diameter of the inner chamber of the cartridge is preferably smaller than or equal to 20 mm.

In the case of storage and mixing systems comprising a dispensing tube, it may also be provided the diameter of the inner chamber of the cartridge is smaller than or equal to 25 mm, and the inside diameter of the dispensing tube is smaller than or equal to 15 mm, wherein the diameter of the inner chamber of the cartridge is preferably smaller than or equal to 20 mm, and the inside diameter of the dispensing tube is smaller than or equal to 12 mm.

As a result of the design of the cartridge, or of the cartridge and of the dispensing tube, according to the invention, it is possible to accommodate both pasty cement components of the PMMA bone cement in a single cartridge, which still allows pressing by way of a manual force application, however which, at the same time, can still be loaded using conventional techniques. With larger diameters, manual force application is no longer readily sufficient for pressing the viscous pasty cement components of the bone cement out of the cartridge. At the described diameters, the advantages of the present invention have a particularly pronounced effect.

According to a preferred refinement of the invention, it may also be provided that two passages are present in the cartridge head, which connect the two cavities to the surrounding area of the storage and mixing system, wherein a removable plug is disposed in each of the passages.

In this way, it is made possible for the cavities to be loaded with the cement components through the passages. In one variant of the present invention, the cement components can also be pressed out through the passages again after the plugs have been removed. In this embodiment, the cartridge head, without the plugs, remains disposed on the front side of the inner chamber of the cartridge even after the dispensing tube has been attached.

In preferred storage and mixing systems, it may also be provided that the cartridge, on the side located opposite the cartridge head, comprises a fastening element for a dispensing device and, on the side of the cartridge head, comprises at least one fastening means, and in particular an external thread, an internal thread, at least one element of a bayonet catch and/or a detent element of a detent closure as fastening means.

In this way, connecting the cartridge to the press-out device at the back side or to a dispensing tube and/or a closure of the cartridge head at the front side is simplified.

The dispensing plungers can be used to simplify the loading of the cavities with the cement components when these are initially seated against the cartridge head. The cement components are pressed into the cavities, and in the process the dispensing plungers are pushed in the direction of the back side of the cartridge, without leaving undesirable trapped air behind in the interior of the cavities, which would interfere with driving the cement components out of the cavities by way of the dispensing plungers. Detent means may be provided, which connect the dispensing plungers to the bending device.

It may furthermore be provided that the cartridge, the cartridge head, the partition, the bending device and the dispensing plungers are made of plastic material, wherein preferred plastic materials are polyethylene co-vinyl alcohol (EVOH), polybutylene terephthalate (PBT), polyethylene terephthalate (PET), and polymethylmethacrylate-co-acrylonitrile.

The composition by way of plastic materials can be implemented in a cost-effective and simple manner. Due to the resistance of the preferred plastic materials to the chemicals present in the cement components, these are particularly well-suited.

Furthermore, it may be provided that the cartridge head is implemented by a rubber-elastic plate, which is fastened to the cartridge by way of a safety cap, wherein the safety cap blocks a movement of the rubber-elastic plate away from the cartridge with the aid of a protruding edge, and wherein the rubber-elastic plate, on the side facing the dispensing plungers, has a recess for accommodating the longitudinal side of the partition, and wherein two regions are preferably defined by this accommodation in the rubber-elastic plate, wherein a passage, which is closed by a plug, is provided in each region.

In this way, an improvement in the sealing action of the storage and mixing system is achieved. The division of the rubber-elastic plate into two regions shall not be understood to mean that the rubber-elastic plate has to comprise two separate parts. The two regions can thus be contiguous and implemented by a single-piece rubber-elastic plate.

It may also be provided that the cartridge head additionally comprises a plastic plate, wherein the plastic plate is disposed on or beneath the rubber-elastic plate in the cartridge head. The plastic plate provides additional sealing and promotes the chemical resistance of the cavities bounded thereby against the cement components. Arranging the additional plastic plate results in an improved diffusion barrier with respect to the methyl methacrylate present in the cement components.

Furthermore, it may be provided that a safety cap is present as a connecting element for connecting the cartridge head to the cartridge, wherein the safety cap comprises an internal thread or an external thread or a bayonet catch or detent elements.

The safety cap is preferably a union nut and can be screwed onto the cartridge. The safety cap can be considered to be part of the cartridge head. In this way, the cartridge head can be connected to the cartridge in a stable manner. The safety cap can be reliably connected to the cartridge by way of the connecting element. This reliably prevents a detachment of the cartridge head from the cartridge during storage and transport.

According to a particularly preferred embodiment of the present invention, it may be provided that the bending device, on the rear side facing away from the cartridge head, has a lateral opening, so that the partition exits the bending device laterally through this opening.

In this way, it is achieved that the partition is guided or steered through the opening, and thus is directed or pushed reliably in the direction of the inside wall of the cartridge, so that the partition does not interfere with the movement of the pusher of the dispensing device, by way of which the dispensing plungers and the bending device are driven, or does not impede this movement.

Moreover, the passage formed by the opening in the bending device can also be used to deform the at least one cut strip of the partition within the bending device.

Moreover, it may be provided that the inclined deflection surface is surrounded by a wall of the bending device in some regions, so that the partition extending through the bending device is bent about the longitudinal axis of the partition by the wall of the bending device surrounding the inclined deflection surface.

The wall can thus be used to deform the partition, so that the same, based on the shape thereof, can be seated more easily against the inside wall of the cartridge or, based on the shape, the risk of an undesirable impairment of the driving motion by way of the pusher of the dispensing device is reduced.

Furthermore, it may be provided that the bending device is designed as an open hollow body, wherein an opening on the back side of the hollow body facing away from the dispensing plungers follows the inner contour of the cartridge in an arc-shaped manner, wherein the length of the arc is greater than or equal to the width of the partition.

It is thus achieved that the bending device, or the open hollow body, deforms the partition such that an undesirable impairment of the advancement of the pusher of the dispensing device, which is used to advance the dispensing plungers and the bending device or the open hollow body, is prevented.

It may be provided that an extension of the partition on the back side of the partition situated opposite the cartridge head exits through the rear opening, and the partition is fixed at this end to at least one point of the cartridge.

This prevents the partition from being undesirably deformed between the cartridge head and the dispensing plungers or between the dispensing tube and the dispensing plungers.

Preferred embodiments of the present invention can also provide that the partition is designed as a panel, which comprises at least one peripheral rubber-elastic seal on the narrow side.

In this way, improved sealing of the cavities with respect to one another is achieved.

The objects underlying the present invention are also achieved by a method for mixing pasty cement components of a pasty cement dough, and in particular of a polymethyl methacrylate bone cement, using a storage and mixing system according to the invention, characterized by the following steps taking place consecutively:

a) removing the cartridge head from the cartridge, or removing at least two plugs from at least two passages in the cartridge head, whereby the cartridge is opened;

b) placing on and connecting a dispensing tube to the opened cartridge, wherein the dispensing tube comprises a mixer;

c) inserting the cartridge into a manually operable dispensing device, the dispensing device comprising an axially advanceable pusher for advancing the dispensing plungers in the cavities of the cartridge;

d) pressing out the pasty cement components with the aid of the dispensing device by axially advancing the dispensing plungers by way of the pusher, whereby the cement components are pushed into the dispensing tube, wherein the two cement components are mixed by the mixer in the dispensing tube to yield the pasty cement dough, and the mixed cement dough flows out of a dispensing opening of the dispensing tube, wherein, synchronously with the movement of the dispensing plungers, the bending device is pushed over the partition into the cartridge, and the partition is pushed by a deflection surface of the bending device in the direction of the inside wall of the cartridge at least so far in the direction of the inside wall of the cartridge that a further movement of the pusher of the dispensing device is not prevented by the partition or is not impaired by the partition.

The steps preferably take place in chronological succession. The dispensing device is preferably driven manually.

The partition is preferably pushed in the direction of the inside wall and deformed so as to be seated against the inside wall of the cartridge after the bending device has been pushed over the partition.

Before the cartridge head has been removed from the cartridge, or the at least two plus have been removed from the at least two passages in the cartridge head, the cartridge or the cavities of the cartridge in which the cement components are stored is or are closed.

It may be provided that the partition is bent in the axial direction by the bending device moving in the direction of the cartridge head, and that, as a result of the bending of the partition, the partition becomes detached from the inside wall of the cartridge, and preferably is dislodged from the guide elements.

It is thus achieved that the bending device is able to initially detach the partition without great effort from the inside wall of the cartridge, and subsequently the bending of the detached partition by way of the deflection surface can likewise take place without great effort. As a result of the reduction in the required effort, it is also possible to use simple manually driven dispensing devices for driving the storage and mixing system according to the invention.

It may furthermore be provided in the method according to the invention that a fixation element fixes the partition to the back side of the cartridge such that an axial movement of the partition in the guide elements in front of the dispensing plungers is prevented.

This prevents the partition from buckling between the dispensing plungers and the cartridge head, or from deforming there, and thereby impeding or making the movement of the dispensing plungers into the cavities more difficult. As an alternative, it could also be provided that the partition is deformed at predetermined bending points and is not fastened to the back side of the cartridge. The partition is then collapsed between the dispensing plungers and the cartridge head or the dispensing tube, and the cement components are driven out in the process. This variant is disadvantageous, however, since defined collapsing in front of the dispensing plungers is more complex to implement than the only minor continuous deformation of the partition with the aid of the bending device.

According to the invention, it may be provided that a connecting element, which connects the cartridge head to the cartridge, is detached so as to remove the cartridge head from the cartridge in step a).

In this way, a more stable connection is achieved between the cartridge head and the cartridge. Moreover, the counterpiece on the cartridge, which is to say a connecting element on the cartridge, can also be used to connect the dispensing tube.

Moreover, it may be provided that the dispensing tube is connected to the cartridge by connecting the connecting element of the dispensing tube to a connecting element of the cartridge.

In this way, it can be ensured that the dispensing tube does not detach from the cartridge when the cement dough is pressed out.

According to the invention, it can furthermore be provided that the pusher of the dispensing device pushes onto the side of the bending device facing away from the dispensing plungers, and the dispensing plungers are driven by way of the bending device.

It is thus achieved that the force available from the pusher can be utilized to an extent as great as possible for advancing the cement components and for deforming and laterally pushing away the partition. This is intended to prevent an excessive portion of the force being used for an undesirable deformation of the cartridge or interfering tilting of the dispensing plungers.

It may also be provided that the side of the bending device facing away from the dispensing plungers comprises an abutment surface for placing thereon the front side of the pusher or of a plate attached thereto, which has the same size as or is larger than the cross-section of the pusher or than the support surface of the plate, wherein the cross-section of the pusher or the support surface of the plate is completely covered by the abutment surface when the pusher is being advanced, or preferably the abutment surface protrudes beyond the cross-section of the pusher or the support surface of the plate, when the pusher is being advanced.

In this way, it is achieved that the movement of the pusher is not impaired by the at least one cut-off strip of the partition.

Preferably, it may also be provided that the dispensing device is manually drivable or is drivable by compressed air or electrically.

Manually drivable dispensing devices are preferred according to the invention, since these do not need to be connected to a compressed air source or an energy source, nor do they have to comprise the same.

The invention is based on the surprising finding that the cement components can be stored in a single shared cartridge having a cylindrical inner chamber if the cement components are separated from one another in the cartridge by a partition, which is disposed in the inner chamber of the cartridge, wherein the two dispensing plungers can be driven by a shared bending device, by way of which the partition is pushed away laterally, so that a further movement of a driving pusher of a dispensing device is not impaired. In this way, it is possible to use manually operated dispensing devices comprising only one pusher since, due to the design according to the invention, the required force is sufficient to advance and mix the cement components and deform the partition and/or to push the partition away against the inside wall of the cartridge, or the required force can be used entirely for these three processes. Due to the design according to the invention, the effort required for advancing the cement components, for mixing the cement components, and for bending the partition away is, in sum, not so much that the dispensing device would overall become sluggish.

Furthermore, surprisingly it was found that in this way a narrow cartridge comprising only a single dispensing plunger can be used to advance the two cement components. The force that is necessary for mixing and driving out the cement components can thus be minimized, so that a dispensing device to be driven by way of manual force can be used together with the storage and mixing system to drive the cement components from the cartridge and mix these with one another.

The invention is based on the idea of using only one cylindrical cartridge, instead of multiple side-by-side cartridges or coaxial cartridges, for the separate storage of the two pasty cement components so as to minimize the flow resistance during dispensation. To avoid two push rods and two plates for driving two dispensing plungers, the cylindrical cartridge is equipped with an axial partition, which divides the inner chamber of the cartridge bounded by two dispensing plungers and a cartridge head into two cavities, in which the two pasty cement components can be stored separately. As a result of bending away or pushing away the partition with the aid of the bending device, it is also possible to use smaller amounts of the PMMA bone cement, and pressing out is also still possible from narrower cartridges comprising inner chambers having smaller inside diameters.

In a first embodiment, the cartridge head is removed and the dispensing tube containing a static mixer is connected directly to the cartridge by way of a connecting element. Immediately thereafter, the cartridge comprising the connected dispensing tube is connected to a manually actuatable dispensing device, or to a manually actuatable applicator, and the dispensation of the cement components or of the cement dough begins. These steps require a time expenditure of approximately 3 to 8 seconds. After approximately 30 seconds of continuous actuation of the press-out device or of the applicator, the dispensation of the cement dough, which is to say of the mixed pasty two-component PMMA bone cement, having a maximum total volume of the two pasty cement components of 60 ml, and preferably of approximately 40 ml, is completed.

In a second embodiment, two plugs are removed from the cartridge head, and the dispensing tube comprising the static mixer is connected to the cartridge by way of a connecting element.

The invention is furthermore based on the idea that a first dispensing plunger is disposed so as to be axially movable in the first cavity and an axially movable second dispensing plunger is disposed in the second cavity. The partition is located between the dispensing plungers. These are connected to one another or are connectable to one another at the back side of the dispensing plungers by way of a bending device. The partition extends through the bending device and is connected to the cartridge behind the bending device. An abutment surface for the pusher of a dispensing device is formed on the back side of the bending device. During the forward movement of the bending device under the action of the pusher in the direction of the cartridge head, or in the direction of an attached dispensing tube, the partition is detached from the inside wall of the cartridge behind the dispensing plunger, is deformed, and is pushed against the inside wall of the cartridge or of the hollow cylinder. For this purpose, the partition is pushed outwardly toward the inside wall of the cartridge by a deflection surface, which is inclined at an angle of approximately 45° with respect to the axis of the cartridge or the movement direction of the bending device. At the same time, the partition is bent on the inner side of the bending device, so that the curvature is parallel to the curvature of the inner side of the cartridge. The partition then exits in a curved manner through a lateral opening on the back side of the bending device parallel to the inner side of the cartridge. The pusher of the dispensing device can thus bear on the support surface of the bending device and press the dispensing plungers across the entire length of the hollow body, pressing out the pasty cement components in the direction of the dispensing tube.

The invention is furthermore based on the observation that a highly viscous cement dough can be dispensed from cylindrical cartridges through a dispensing tube comprising a static mixer in an acceptable time and with a force expenditure that is acceptable, as it can be applied manually, using commercially available, manually drivable dispensing devices or applicators, if the dispensing plunger has a maximum diameter of 25 mm at the end face. As a result of the design according to the invention, a cartridge system is provided that is able to implement such small diameters for the application of high-viscosity cement components. The cartridge or the cavities can nonetheless be loaded with the cement components without great effort.

An exemplary storage and mixing system according to the invention for pasty two-component polymethyl methacrylate bone cement is composed of:

a) a tubular cartridge;
b) two guide elements, which are disposed parallel to the longitudinal axis of the cartridge in or on the inside wall of the cartridge;
c) a partition that is disposed axially in the tubular cartridge and in a form-locked manner engages in the two guide elements, which are disposed in or on the inside wall of the cartridge, wherein the partition divides the cavity of the cartridge into a first cavity, in which a first pasty cement component is present, and a second cavity, in which a second pasty cement component is present;
d) a cartridge head, which closes one end of the tubular cartridge, wherein a receptacle for the end face of the partition is provided on the bottom side of the cartridge head;
e) a dispensing tube comprising a fastening means for fastening to the cartridge;
f) a half moon-shaped or circular segment-shaped first dispensing plunger, which is axially movable in the first cavity;
g) a half moon-shaped or circular segment-shaped second dispensing plunger, which is axially movable in the second cavity;
h) a bending device, which is designed as an open hollow body, which on the front side is connected to the back side of the first dispensing plunger and the back side of the second dispensing plunger, wherein the distance between the first dispensing plunger and the second dispensing plunger is equal to or greater than the thickness of the partition, and wherein a support surface for the pusher of a press-out device is disposed on the back side of the bending device;
i) wherein a lateral opening on the back side of the hollow body is provided in the direction of the cartridge bottom, the opening following the inner contour of the cartridge in an arc-shaped manner, wherein the length of the arc is greater than or equal to the height of the partition;
j) wherein the portion of the strip-shaped partition facing the cartridge bottom is disposed between the dispensing plungers and/or exits the opening of the hollow body in the form of a strip that is bent perpendicularly to the longitudinal axis, wherein the curvature of the strip-shaped partition follows the curvature of the cavity of the cartridge, and
k) wherein the bent, strip-shaped partition exiting the opening of the hollow body is fixed to the inner side of the cartridge in at least one point.

An opening is present on the back side of the hollow body in the direction of the cartridge bottom. This opening follows the inner contour of the cartridge in an arc-shaped manner, wherein the length of the arc is greater than or equal to the height of the partition. The portion of the strip-shaped partition facing the cartridge bottom, which exits between the first dispensing plunger and the second dispensing plunger on the back side of the dispensing plungers, is bent by the hollow body so as to exit the guide elements, and a strip that is bent perpendicularly to the longitudinal axis exits the opening of the hollow body provided on the back side. The curvature of the strip-shaped partition follows the curvature of the cavity of the cartridge. The exiting, bent strip-shaped partition is fixed to the inner side of the cartridge in at least one point. During a forward movement of the bending device in the direction of the cartridge head, this prevents the partition from collapsing. When the two pasty cement components are pressed out through the dispensing plungers having a half moon-shaped or circular segment-shaped cross-section, the partition is dislodged behind the dispensing plungers by the bending device designed as a hollow body, is bent and pressed against the inner side of the cartridge, so that the pusher can press the bending device, and thus the dispensing plungers, in the direction of the cartridge head or in the direction of the dispensing tube without impairment.

According to the invention, it may be provided that axial recesses are present on the inner side of the cartridge, serving as guide elements. Alternatively, axial ribs or protrusions can also be provided on the inside wall of the cartridge as guide elements for the partition.

A linear recess is preferably present on the upper end face of the cartridge head, wherein the ends of the recesses are seated against one another at the two recesses of the cartridge. According to the invention, alternatively a rib can also be disposed on the upper end face of the cartridge head, the ends of the rib being seated against the axial ribs of the cartridge.

The partition is designed as a panel, for example, which comprises at least one peripheral rubber-elastic seal on the narrow side.

The partition divides the cavity formed by the inside wall of the cartridge, the dispensing plungers and the cartridge head into the first cavity and the second cavity in a manner impervious to liquid.

The pasty cement components comprise the highly volatile monomer methyl methacrylate, which can be polymerized by radical polymerization. For storing the cement components, it is thus indispensable for the cartridge, the cartridge head, the partition and the dispensing plunger to be made of plastic materials that represent a good diffusion barrier for methyl methacrylate. According to the invention, it may thus be provided that the cartridge, the cartridge head, the partition and the dispensing plunger are made of plastic material, wherein preferred plastic materials are polyethylene co-vinyl alcohol (EVOH), polybutylene terephthalate (PBT), polyethylene terephthalate (PET), and polymethylmethacrylate-co-acrylonitrile. Additionally, it is also possible to apply diffusion-resistant metal layers, metal oxide or metalloid oxide layers or plastic layers to the parts that do not come in contact with the cement components. In particular, aluminum layers can be used as metal layers. Suitable metalloid oxide layers are in particular silicon dioxide layers.

The cartridge, for example, comprises a fastening element for a press-out device at one end and comprises at least one external thread and/or one internal thread and/or at least one element of a bayonet catch and/or at least one detent element of a detent closure as a connecting element at the opposite end.

The cartridge head is formed of a rubber-elastic plate and a safety cap made of plastic material, wherein the safety cap blocks the rubber-elastic plate toward the top by way of a protruding rim, and wherein the rubber-elastic plate has two openings, which are closed by plugs.

In a first embodiment, a plastic plate having two openings that can be closed by way of plugs is disposed on or beneath the rubber-elastic plate in the cartridge head.

Serving as a connecting element, the safety cap comprises an internal thread or an external thread or a bayonet catch or detent element for a latchingly engaging closure.

According to the invention, a static mixer is disposed in a dispensing tube. An internal thread and/or an external thread and/or elements of a bayonet catch and/or detent elements of a detent closure are attached to the base of the dispensing tube as connecting means.

In an alternative embodiment, the end face of the cartridge is designed as a cartridge head, wherein two openings that can be closed by plugs break through the end face of the cartridge.

For example, a method for mixing the pasty cement components of the pasty polymethyl methacrylate bone cement, using the storage and mixing system, is also according to the invention. The method is characterized by the following steps taking place consecutively:

a) removing the cartridge head from the cartridge, or opening the cartridge by removing at least one plug in the cartridge head;

b) connecting a dispensing tube, which comprises a static mixer, to the opened cartridge;

c) connecting the cartridge to a manually actuatable applicator;

d) manually actuating the press-out device, wherein the pusher pushes on the support surface, wherein the pasty first cement component is pressed from the first cavity through the first dispensing plunger having a circular segment-shaped or half moon-shaped cross-section, and the pasty second cement component is pressed from the second cavity through the second dispensing plunger having a circular segment-shaped or half moon-shaped cross-section, into the dispensing tube and the static mixer, wherein the mixed cement dough exits at the dispensing opening of the dispensing tube;

e) wherein, synchronously with the advancement movement of the dispensing plungers parallel to the partition, the hollow body, serving as the bending device behind the dispensing plungers, dislodges the partition from the guide elements by bending the partition, wherein the bent partition is seated against the inner side of the cartridge parallel to the inner side of the cartridge next to the support surface; and f) wherein the fixation element on the cartridge bottom fixes the partition removed from the guide elements such that an axial movement of the partition in the guide elements in front of the dispensing plungers is prevented.

In one variant of the present method, a press-out device driven by way of compressed air or electrical current is used in steps d) and e) instead of the manually driven press-out device.

BRIEF DESCRIPTION OF THE DRAWINGS

Further exemplary embodiments of the invention will be described hereafter based on thirteen schematically illustrated figures, however without thereby limiting the invention. In the drawings.

DETAILED DESCRIPTION OF THE DISCLOSURE

Figure 1:
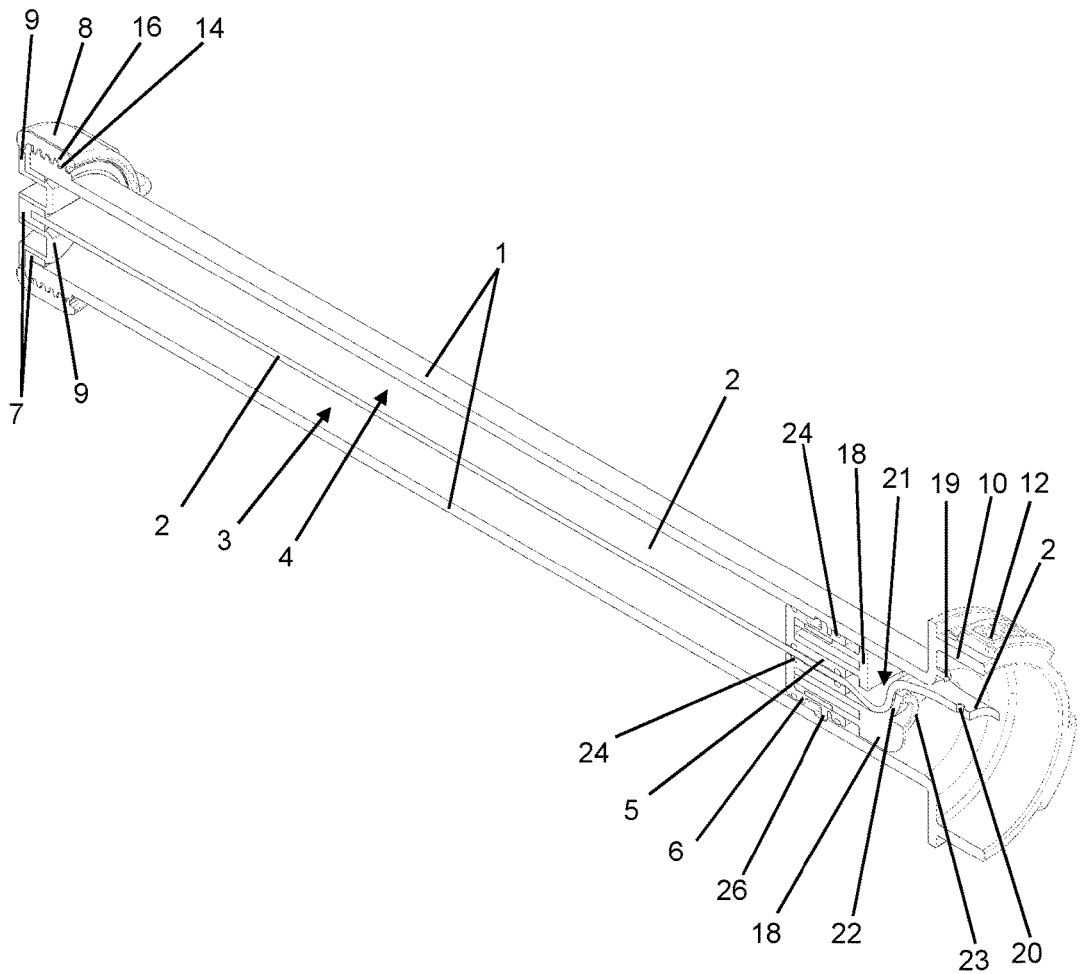
FIG. 1 shows a schematic perspective cross-sectional view of a storage and mixing system according to the invention.

For the sake of simplicity, identical and like components of different embodiments in the figures are in part denoted by the same reference numerals.

FIG. 1 shows a schematic perspective cross-sectional view of a storage and mixing system according to the invention. The storage and mixing system comprises a cylindrical cartridge 1 as a central component, in which a partition 2 connects two opposing inner sides of the inside wall of the cylindrical cartridge 1. The cartridge 1 and the partition 2 are designed in one piece as a joint injection-molded part, and the edges of the partition 2 are each connected to the cylindrical inside wall of the cartridge 1 by way of a predetermined breaking point, such as a taper or another weakening of the material that can be easily severed, for example. It may also be provided that the partition 2 is seated against the inside wall of the cartridge 1 and thus is not connected in one piece to the cartridge 1. In the latter case, however, care must be taken to ensure that the edge of the partition 2 is hermetically sealed with respect to the inside wall of the cartridge 1. The partition 2 and the cartridge 1 are then two separate parts. In any case, the partition 2 divides the inner chamber of the cartridge 2 into two separate cavities 3, 4 that are separated from one another in a fluid-tight manner and in which the two pasty starting components of a PMMA bone cement are stored.

Figure 5:
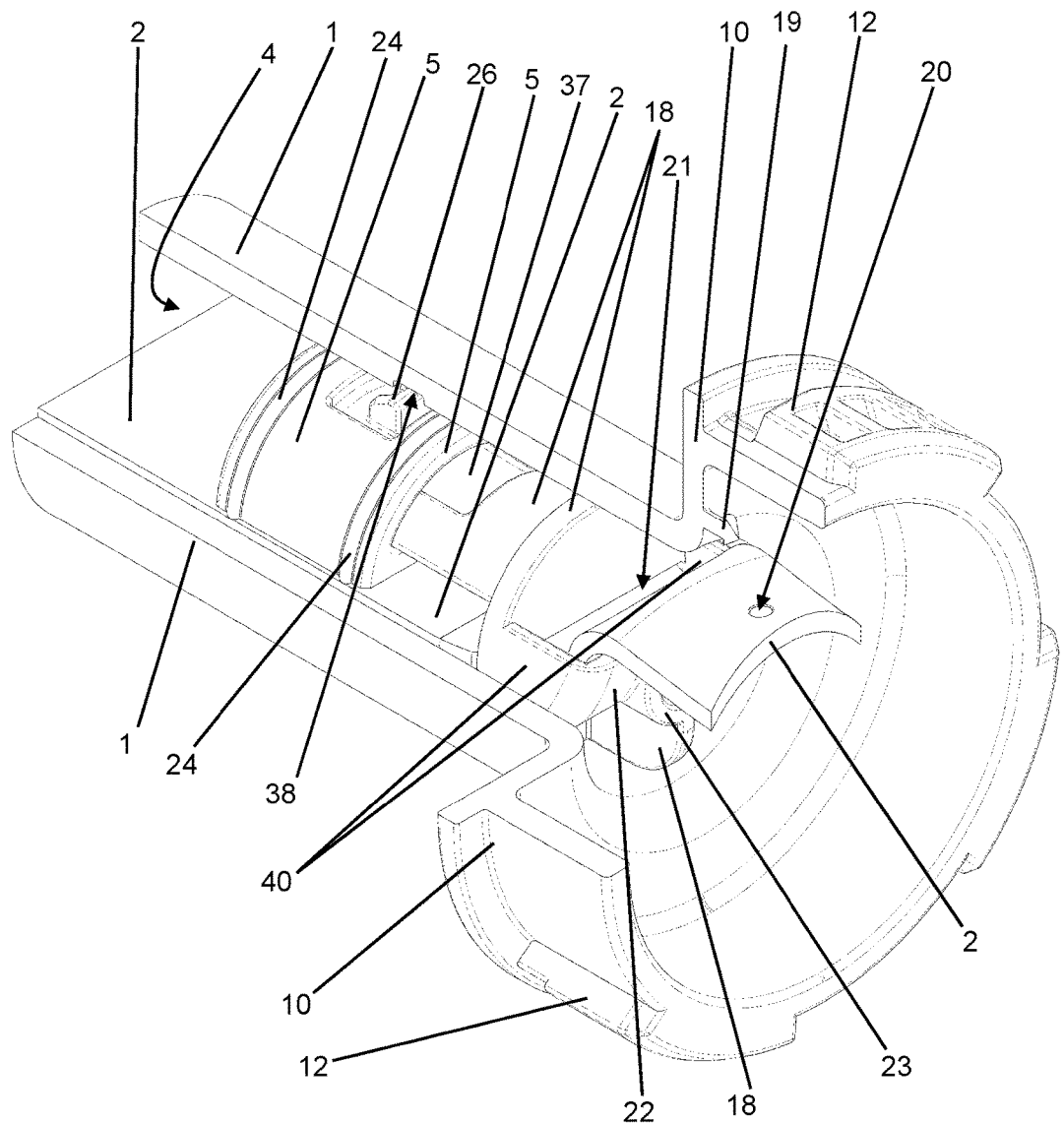
FIG. 5 shows an enlarged schematic perspective cutaway view of the cartridge bottom of the storage and mixing system according to the invention of FIG. 4, comprising latchingly engaged dispensing plungers and the inserted bending device, into which the partition fed.
Figure 12:
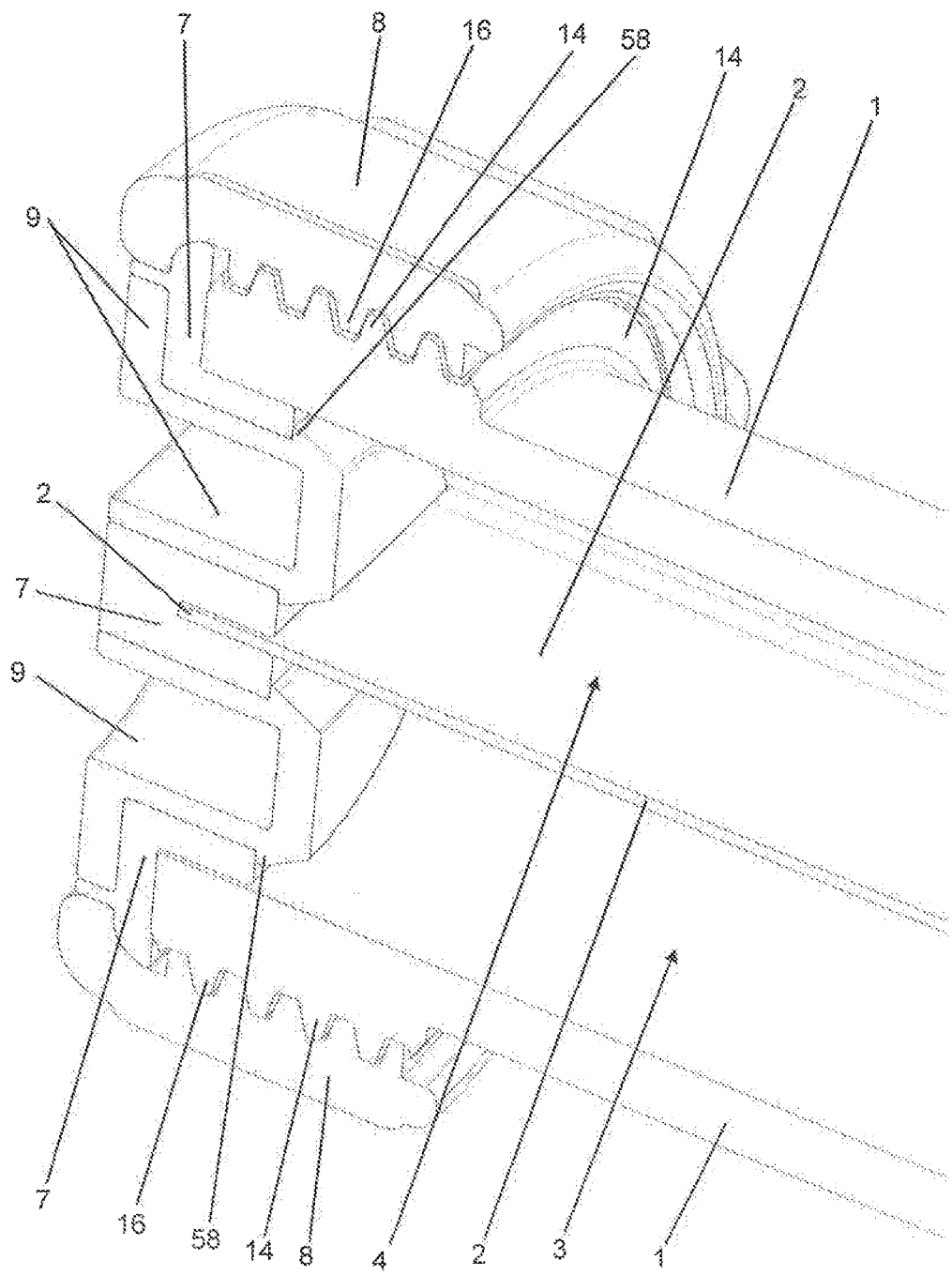
FIG. 12 shows a schematic perspective cross-sectional view of the front portion of the storage and mixing system according to the invention of FIGS. 1 and 4 to 7, and of FIGS. 8 to 11.

On the back side (on the right in FIG. 1), the cavities 3, 4 are bounded by two dispensing plungers 5, 6, wherein the dispensing plungers 5, 6 can be axially displaced in the two cavities 3, 4. FIG. 5 shows a detailed view in the form of an enlarged schematic perspective partial cross-sectional view of the cartridge bottom of the storage and mixing system according to the invention of FIG. 1. At the front side of the storage and mixing system situated opposite the dispensing plungers 5, 6, the two cavities 3, 4 are closed by a cartridge head 7 in the form of a rubber-elastic plate 7. The cartridge head 7 is fastened to the front side of the cartridge 1 by way of a union nut 8 made of plastic material. Two passages are provided in the cartridge head 7, each being closed by a plug 9. The cavities 3, 4 can be accessed through the two passages when the plugs 9 are not inserted therein. FIG. 12 shows a schematic perspective cross-sectional view of the front portion of the storage and mixing system according to the invention as a detailed view, wherein the storage and mixing system in FIG. 12 is closed by the cartridge head 7 and the plug 9 therein, as in FIG. 1.

On the back side of the cartridge 1 or on the bottom side (on the right in FIG. 1), a connector 10 comprising fastening elements 12 is disposed on the cartridge 1. The cartridge 1 can be connected to a dispensing device or an applicator (not shown in FIG. 1) by way of the connector 10 and the fastening elements 12. On the opposite front side (on the left in FIG. 1) of the cartridge 1, the cartridge head 7 is fastened by way of the union nut 8 in that an internal thread 16 of the union nut 8 is screwed onto an external thread 14 on the cartridge 1. The rubber-elastic plate 7, or the cartridge head 7, seals the cavities 3, 4 toward the front.

The cartridge 1 has an outside diameter of 22 mm, an inside diameter of 20 mm, and a length of approximately 18 cm.

The two dispensing plungers 5, 6 are connected to one another at the back sides by way of a bending device 18. To this end, the bending device 18 extends with two cylinder segment-shaped ends pointing in the direction of the cartridge head 7 into matching cavities in the back sides of the dispensing plungers 5, 6. The partition 2 extends through the bending device 18, or is fed through the bending device 18. In the region of the connector 10, a mushroom-shaped pin 19 having a tip is provided on the cartridge 1 as a fastening element 19 for fastening the partition 2. In the rearmost portion of the partition 2, which is disposed behind the bending device 18 (on the right in FIG. 1), a hole 20 is present in the partition 2. The pin 19 can be placed through the hole 20 so as to fasten the partition 2 to the cartridge 1, or to the cartridge bottom, or to the connector 10 of the cartridge 1. This prevents the partition 2 from being deformed or buckling in front of the dispensing plungers 5, 6 when the dispensing plungers 5, 6 are driven forward in the cavities 3, 4 (to the left in FIG. 1).

The bending device 18 closes the inner chamber of the cartridge 1 toward the back, with the exception of the passage for the partition 2. For this purpose, the bending device 18 has a cylindrical shape in some regions (see also FIG. 3). The partition 2 is guided through the passage in the bending device 18, exiting through a lateral opening 21 in the bending device 18, which guides the partition 2 in the direction of the inside wall of the cartridge 1. The partition 2 is introduced through a gap into the bending device 18 on the other side of the passage through the bending device 18. A portion of the passage through the bending device 18 is bounded by a deflection wall 22 that is inclined with respect to the axis of the cartridge 1 and the partition 2 and that deflects, and thereby deforms, the partition 2 in the direction of the inside wall of the cartridge 1. On the inner side in the passage of the bending device 18, the deflection wall 22 forms an inclined deflection surface (see FIG. 10, reference numeral 50), which is oriented in the direction of the gap. An abutment surface 23 for a pusher of a dispensing device (not shown in FIG. 1) is formed on the back side of the bending device 18. A rib of the bending device 18 and the tube section in front of the abutment surface 23 ensure mechanical stability of the bending device 18 and are able to absorb forces that arise during the deformation of the partition 2 when the partition 2 is driven by the bending device 18.

The dispensing plungers 5, 6 are each sealed by two peripheral seals 24 made of rubber with respect to the inside wall of the cartridge 1 and with respect to the partition 2. The dispensing plungers 5, 6 are each connected to a releasable detent element 26 having suitable mating detent elements (in the form of two depressions) in the inside wall of the cartridge 1. The dispensing plungers 5, 6 can be pushed by way of pressure from the back side of the cartridge 1 (from the right in FIG. 1) in the direction of the front side of the cartridge 1 (on the left in FIG. 1), which is to say in the direction of the cartridge head 7. The detent elements 10 can be readily released by the application of pressure to the bottom of the dispensing plungers 5, 6 when the cartridge head 7 is removed, or at least when the plugs 9 are removed. The detent elements 10 are primarily used to prevent the dispensing plungers 5, 6 from being pressed out of the cartridge 1 at the bottom when the cavities 3, 4 of the cartridge 1 are being loaded with the cement components, or from being pressed beyond the desired position defined by the mating detent elements in the inside wall of the cartridge 1 in the direction of the cartridge bottom (on the right in FIG. 1).

Figure 2:
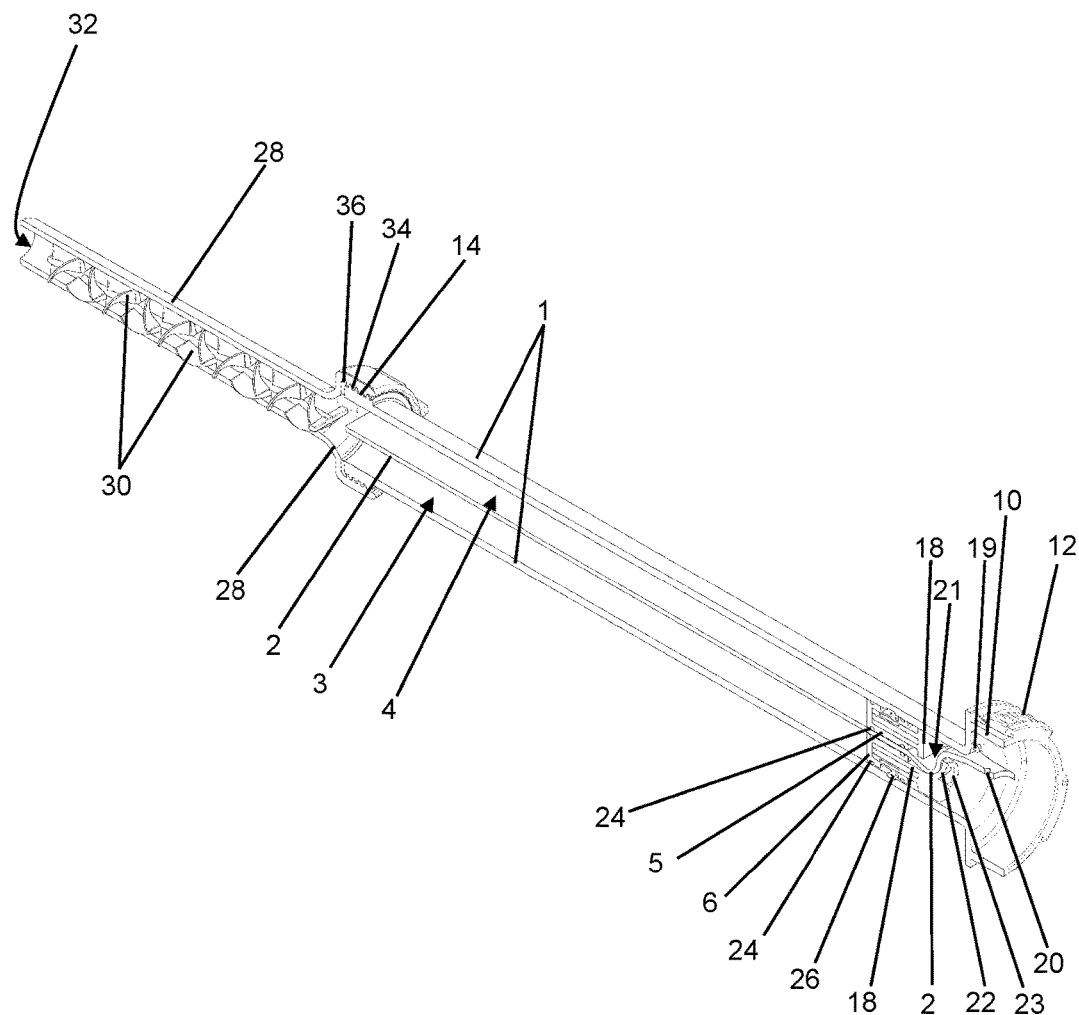
FIG. 2 shows a schematic perspective cross-sectional view through the storage and mixing system according to the invention of FIG. 1 immediately prior to the application of the PMMA bone cement, in which a dispensing tube is attached to the cartridge.

FIG. 2 shows a schematic perspective cross-sectional view through the storage and mixing system according to the invention of FIG. 1, immediately prior to the application of the PMMA bone cement, in which a dispensing tube 28 is screwed onto the external thread 14 of the cartridge 1. A static mixer 30, including a plurality of twists and mixing elements for mixing the cement components, is provided in the dispensing tube 28. The dispensing tube 28 can be even longer than the dispensing tube 28 shown in FIG. 2 so as to make regions that are difficult to access easier to reach, as may be helpful during hip surgeries, for example (see FIG. 3 in this regard, for example). FIG. 2 shows all parts, except for the static mixer 30, in a sectional view, while the static mixer 30 is shown in a perspective illustration and protrudes from the cutting plane.

The cement components are mixed by being pressed through the dispensing tube 28, and thus through the static mixer 30. The cement dough thus produced and mixed exits via a dispensing opening 32 at the tip of the dispensing tube 28. The dispensing tube 28 includes an internal thread 34, which fits onto the external thread 14 of the cartridge 1, so that the dispensing tube 28 can be connected to the cartridge 1 in a stable and strong manner. A sealing ring 36 is disposed between the dispensing tube 28 and to the front side of the cartridge 1 to prevent the cement components from leaking between the dispensing tube 28 and the cartridge 1. A pressure-stable and pressure-tight connection between the dispensing tube 28 and the cartridge 1 is achieved by way of the threads 14, 34 and the sealing ring 36.

The advancement of the dispensing plungers 5, 6 is generated by a dispensing device (not shown in FIG. 2), which is connected to the connector 12 and by way of which a pusher (see FIGS. 8 to 11, reference numeral 44) or a push rod of the dispensing device is manually drivable in the direction of the dispensing tube 28. The pusher then pushes onto the abutment surface 23, so that the dispensing plungers 5, 6 are advanced in the direction of the dispensing tube 28, and additionally the bending device 18 is driven into the cartridge 1, wherein the partition 2 is pushed through the passage in the bending device 18 and is deformed in the process, and is deflected by way of the deflection surface (see FIG. 9). The pressure of the pusher releases the detent elements 10 and drives the dispensing plungers 5, 6 forward. The dispensing plungers 5, 6 are hermetically sealed with respect to the inside walls of the cartridge 1 and the partition 2. In this way, the content of the cavities 3, 4 of the cartridge 1, which is to say the two pasty cement components present, can be driven forward and out through the dispensing tube 28.

Figure 3:
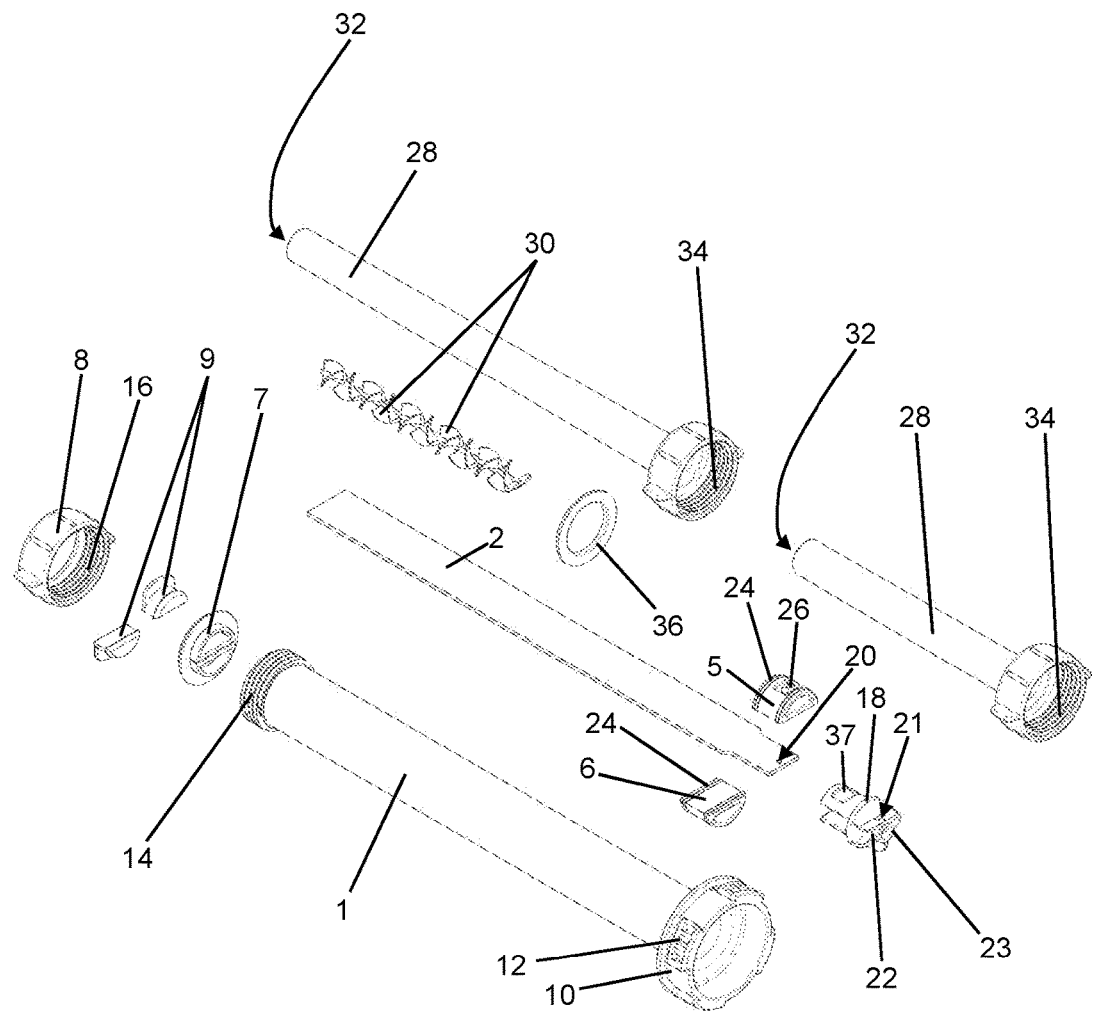
FIG. 3 shows a schematic perspective exploded view of storage and mixing systems according to the invention comprising two different alternative variants for the dispensing tubes.

FIG. 3 shows a schematic perspective exploded view of storage and mixing systems according to the invention comprising two alternative and different dispensing tubes 28. The composition of the storage and mixing systems is analogous to the above-described storage and mixing system.

FIG. 3 shows two alternative variants of the dispensing tubes 28 having differing lengths. The longer dispensing tube 28 can be used to access also regions that are difficult to reach during surgery. This may be advantageous when inserting an artificial hip, for example.

The cartridge head 7 illustrated in FIG. 3 includes two circular segment-shaped or half moon-shaped passages, which can be closed by suitable plugs 9. A plug 9 can be inserted and latchingly engaged in each of the two passages. The rubber-elastic plate 7 and the plugs 9 are suitable for assembling cartridge heads 7 of storage and mixing systems according to the invention. Other rubber-elastic plates 7 are also conceivable, which can differ with respect to the shapes of the passages thereof and the shapes of the plugs 9 that close these passages. In the shown variant, the passages and the plugs 9 have a semi-circular or half moon-shaped cross-section. In one variant, which is not shown, the passages and the plugs 9 have a circular cross-section. In the shown variant, the free cross-section for loading the two cement components is larger than in the variant not shown. In the variant not shown, the geometry is adapted to loading pipes or syringes (likewise not shown), by way of which the cavities 3, 4 are loaded with the cement components, so that the loading pipes or syringes are hermetically sealed with respect to the passages. The plugs 9 can also be removed in order to dispense the cement components from the cavities 3, 4 of the cartridge 1 again, if the entire cartridge head 7 is not supposed to be removed.

A flat plastic disk (not shown) may be placed onto the rubber-elastic plate 7 on the side pointing into the inner chamber of the cartridge 1. This plastic disk is used to stabilize the shape of the rubber-elastic plate 7 on the one hand, and to improve the chemical stability of the receptacle or of the cavities 3, 4 for the cement components on the other hand.

The assembly of the tubular cartridge 1 comprising the partition 2, the connector 10, the fastening elements 12 and the external thread 14 has the same shape in all variants. Both the union nut 8 and the dispensing tube 28 can be screwed onto the external thread 14 of the cartridge 1. Variants in which the rubber-elastic plate 7 is fixedly connected to the cartridge 1, or not designed in a rubber-elastic manner and/or in one piece with the cartridge 1, are also conceivable. In this way, no union nut 8 is required, and the dispensing tube 28 can simply be screwed onto the cartridge 1 after the plugs 9 have been removed. The cement components can then simply be pressed through the passages into the dispensing tube 28, where they are mixed by way of the static mixer 30 to yield the desired cement dough.

FIGS. 4 to 7 show schematic, partially cutaway perspective views and a cross-sectional view of the cartridge bottom of the storage and mixing system according to the invention of FIGS. 1 and 2 in different stages during the assembly of the storage and mixing device. Depressions 37, which engage in detents (not shown) in the interior of the dispensing plungers 5, 6, are provided as mating detents 37 in the two cylinder segment-shaped legs of the bending device 18, which are inserted into the intended cavities in the dispensing plungers 5, 6 so as to connect these to the bending device 18 and thus to one another. The depressions 37 are apparent particularly well in FIGS. 4 and 5.

Figure 4:
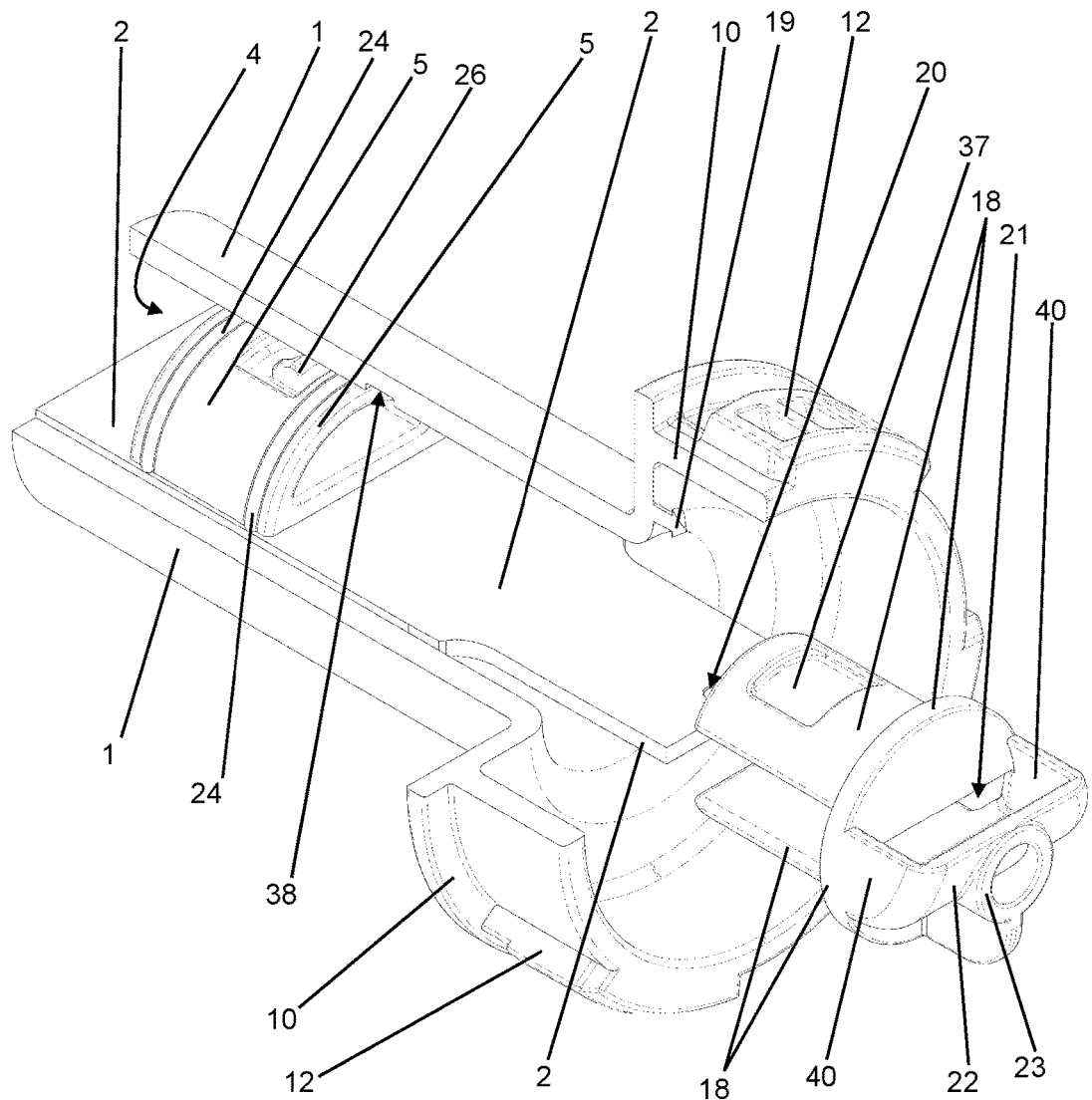
FIG. 4 shows an enlarged schematic perspective cutaway view of the cartridge bottom of the storage and mixing system according to the invention of FIGS. 1 and 2, with the bending device not being inserted yet.

In FIG. 4, the bending device 18 has not yet been inserted into the bottom of the cartridge 1, and the dispensing plungers 5, 6 have not yet latchingly engaged in the end positions thereof. The detent means 26 of the dispensing plungers 5, 6 engage in depressions 38 in the inside wall of the cartridge 1 when they are pushed sufficiently deep in the direction of the back side of the storage and mixing system (on the right in FIGS. 4 and 7) into the cavities 3, 4 of the cartridge 1. The detent means 26 block any further movement of the dispensing plungers 5, 6 in the direction of the back side of the storage and mixing system, while the latching engagement can be released during a movement in the direction of the cartridge head 7.

In the position shown in FIG. 5, the dispensing plungers 5, 6 are latchingly engaged with the detent means 26 in the depressions 38, and the bending device 18 has been inserted into the bottom of the cartridge 1, so that the cylinder segment-shaped legs of the bending device 18 have already been pushed to some degree into the intended openings in the dispensing plungers 5, 6. The partition 2 is fed through the passage in the bending device 18 and extends through the lateral opening 21. The feeding of the partition 2 has caused the same to become deformed. Initially, the partition 2 is bent perpendicularly to the center line thereof in the direction of the inside wall of the cartridge 1. Afterwards, the partition 2 was bent about the axis thereof. The inclined deflection wall 22 is flanked on both sides by two walls 40, which laterally support the deflection wall 22 and form lateral walls 40 of the passage. As a result of the walls 40, the partition 2 is bent about the axis of the partition 2.

Figure 6:
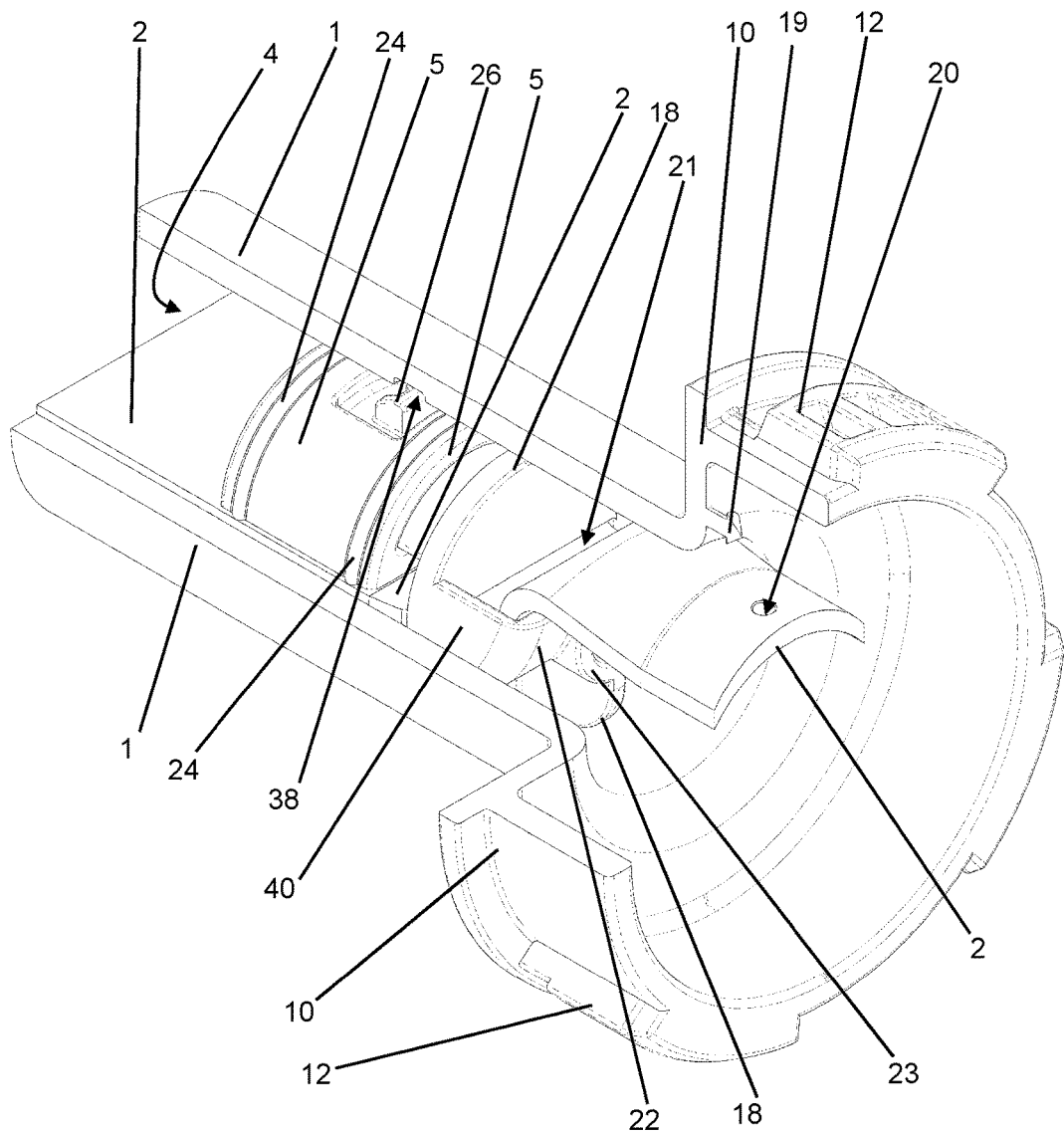
FIG. 6 shows an enlarged schematic perspective cutaway view of the cartridge bottom of the storage and mixing system according to the invention of FIGS. 4 and 5, in which the bending device is connected to the dispensing plungers.
Figure 7:
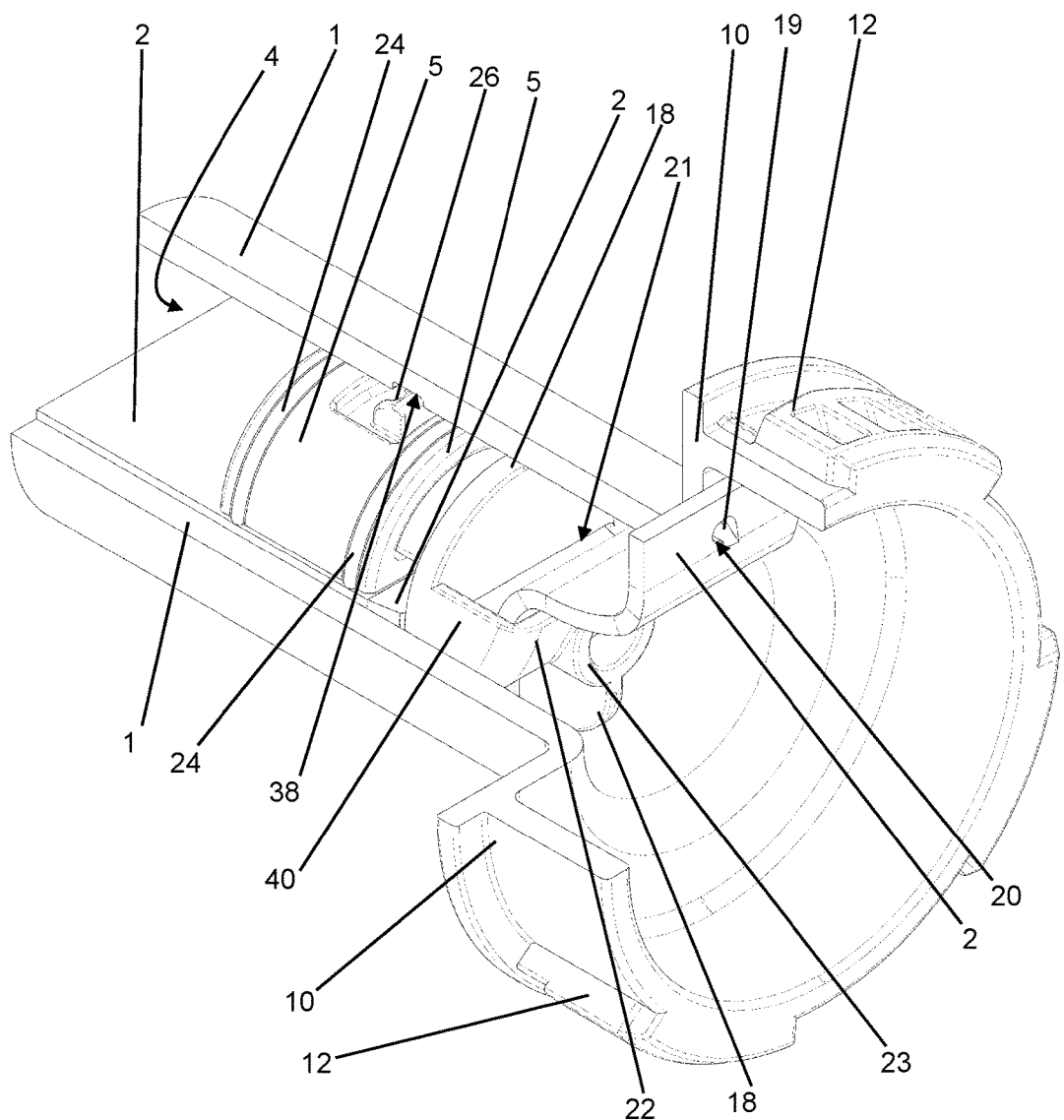
FIG. 7 shows an enlarged schematic perspective cutaway view of the cartridge bottom of the storage and mixing system according to the invention of FIG. 6, in which the partition is fixed to the cartridge behind the bending device.

In the position shown in FIG. 6, the dispensing plungers 5, 6 are latchingly engaged with the detent means 26 in the depressions 38, and the bending device 18 has been inserted completely of the dispensing plungers 5, 6 at the bottom and connects these. Thereafter, the partition 2 can be pushed with the hole 20 onto the pin 19 so as to fix the partition 2 to the cartridge 1. This state is shown in FIG. 7. The storage and mixing system is thus ready for use. The front side of the storage and mixing system is closed by the cartridge head 7 and the plugs 9. In this state, the storage and mixing system can be used to store the cement components, and it can be delivered to the user in this state. This state is thus particularly preferred according to the invention.

So as to use the storage and mixing system according to the invention, this must now be rendered operational. For this purpose, a storage and mixing system according to the invention is illustrated in FIGS. 8 to 11. This exemplary embodiment corresponds to those according to the preceding FIGS. 1 to 7, wherein a mushroom-shaped pin 19 having no tip, which is to say having a rounded cap, is provided on the cartridge 1 as a fastening means 19 for fastening the partition 2. Since this is only a small and insignificant difference, the method described hereafter can be readily applied to the embodiments according to FIGS. 1 to 7, 12 and 13.

Figure 8:
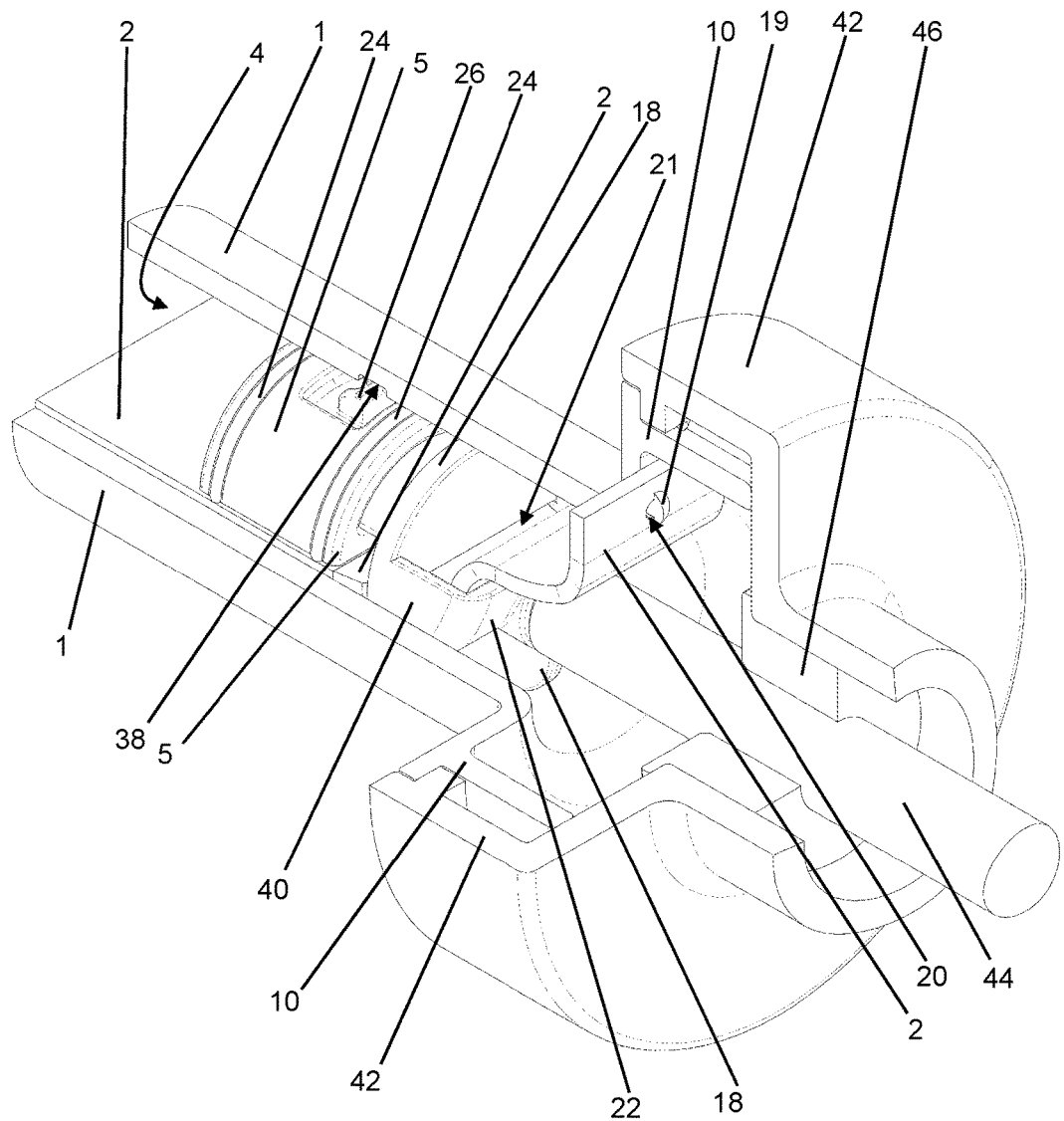
FIG. 8 shows a schematic perspective cutaway view of a cartridge bottom of a storage and mixing system according to the invention, which is inserted in a dispensing device for implementing a method according to the invention.
Figure 9:
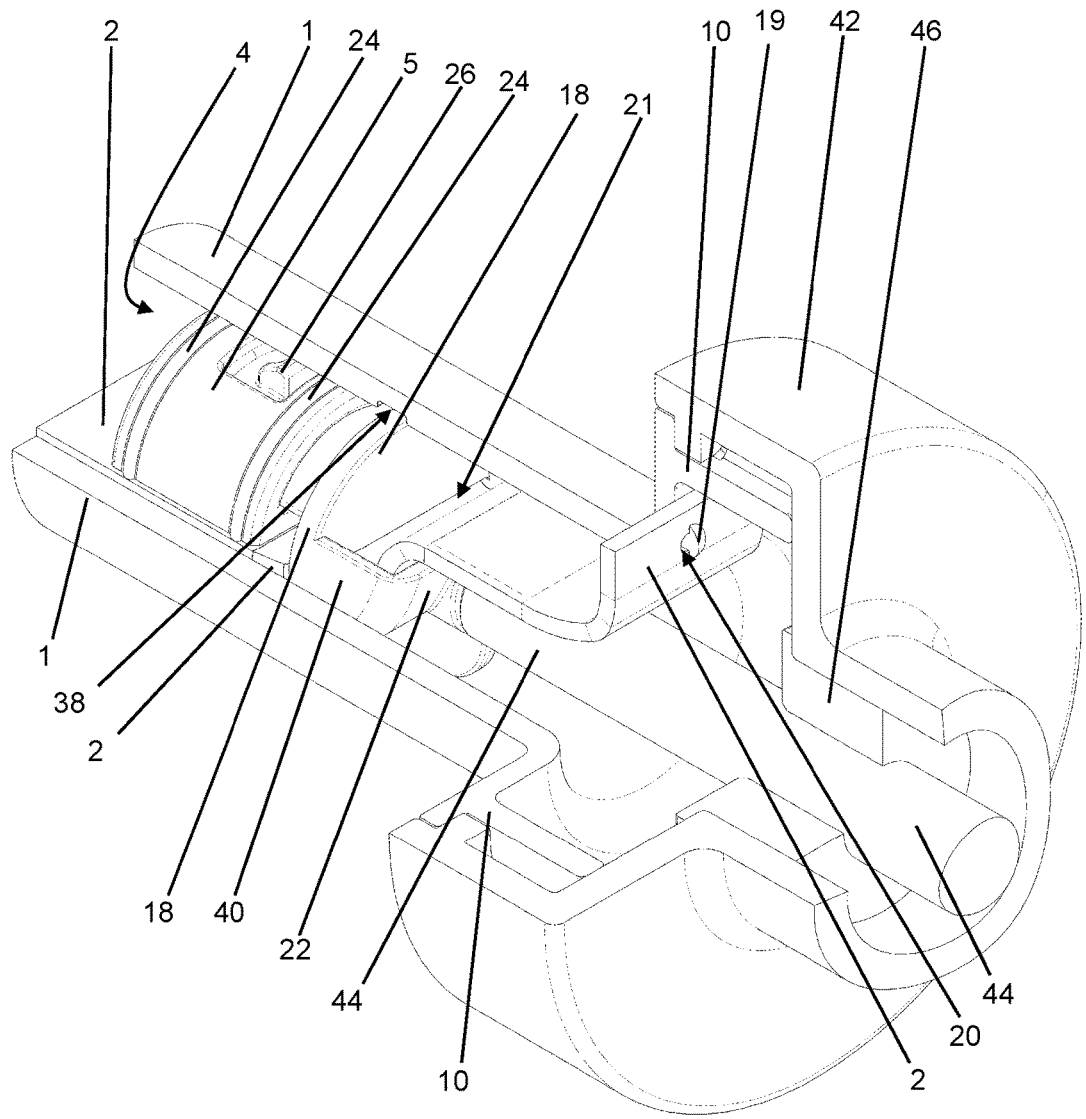
FIG. 9 shows a schematic perspective cutaway view of the cartridge bottom of the storage and mixing system according to the invention of FIG. 8, in which the pusher of the dispensing device has driven the bending device and the dispensing plungers forward.
Figure 10:
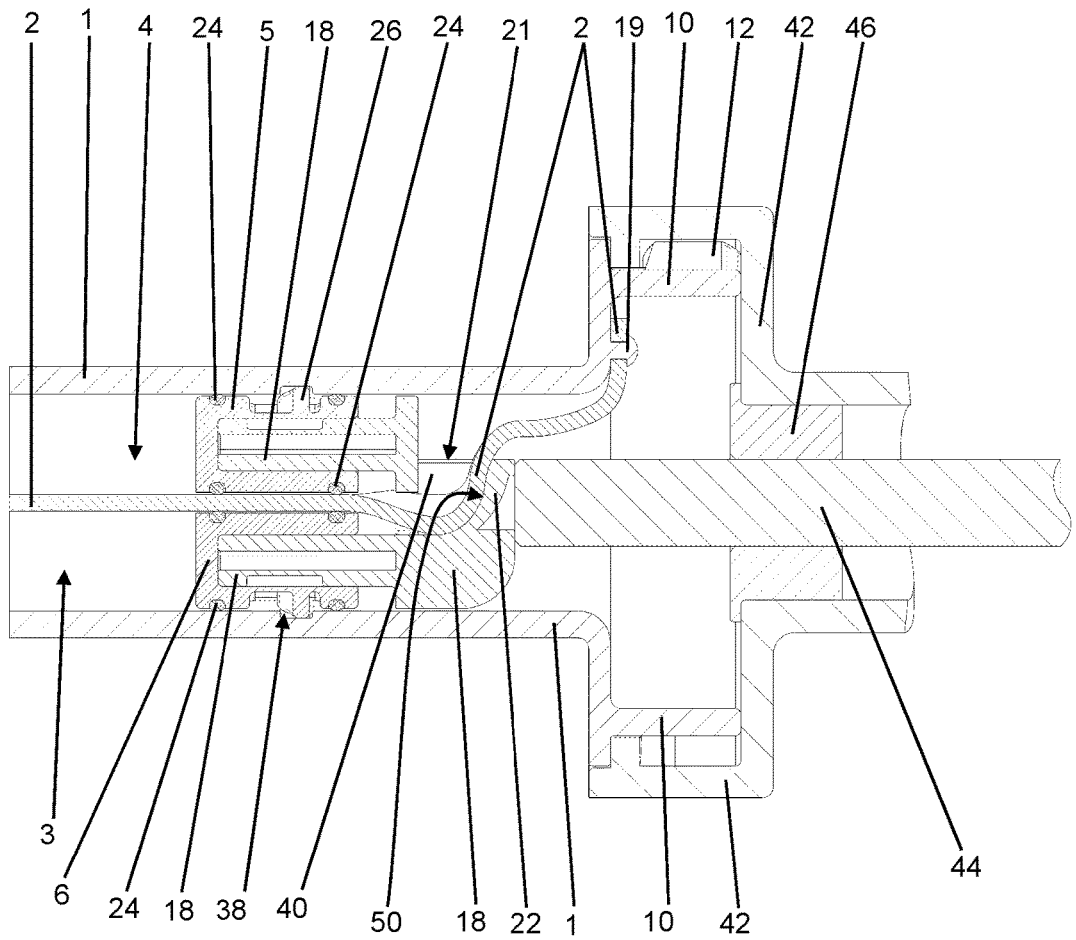
FIG. 10 shows a schematic cross-sectional view of the cartridge bottom of the storage and mixing system according to the invention of FIG. 8.
Figure 11:
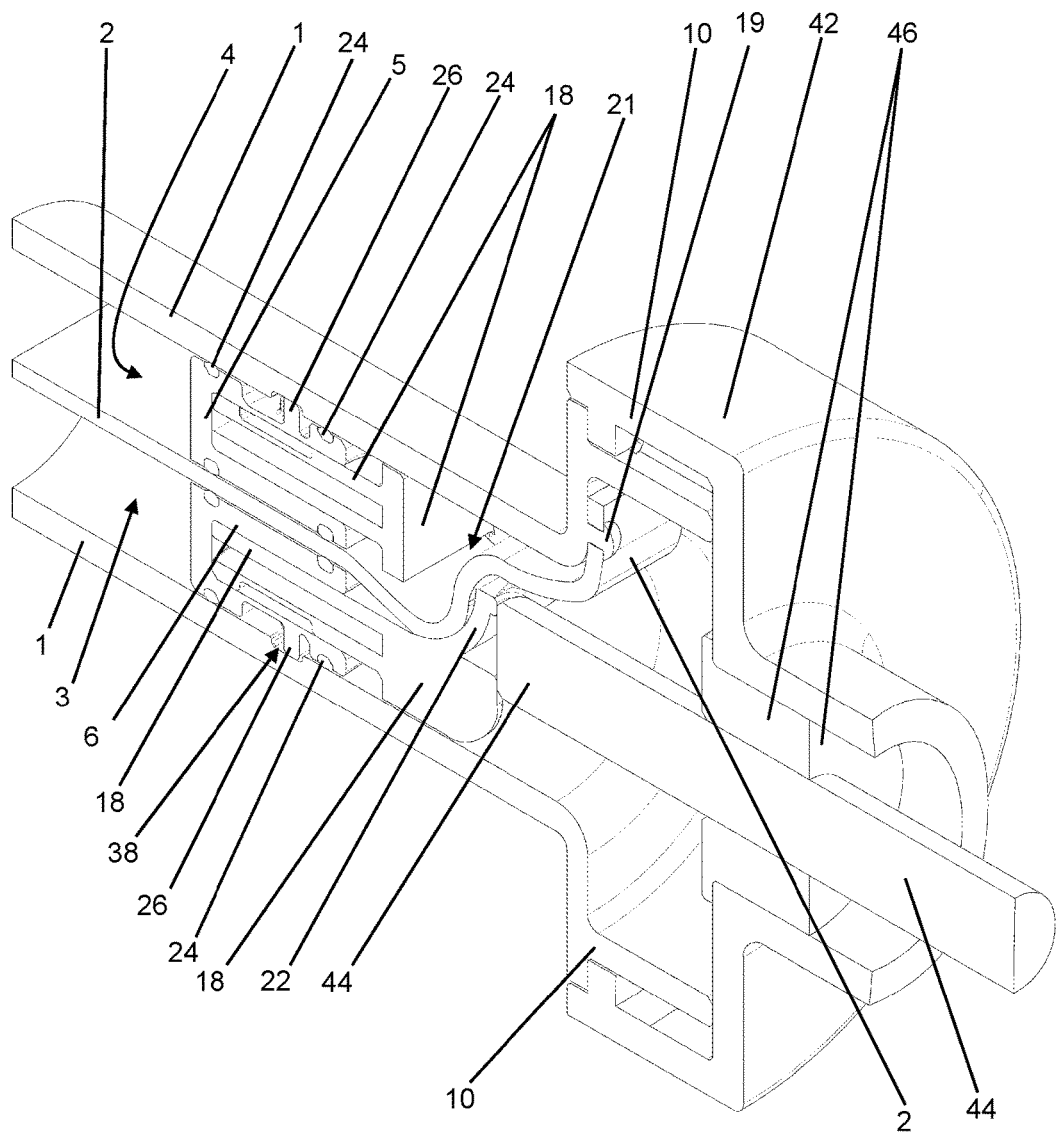
FIG. 11 shows a schematic perspective cross-sectional view of the cartridge bottom of the storage and mixing system according to the invention of FIG. 8.

FIG. 8 shows a schematic perspective cutaway view of a cartridge bottom of a storage and mixing system according to the invention, which is inserted in a dispensing device for implementing a method according to the invention, FIG. 9 shows a schematic perspective cutaway view of the cartridge bottom of the storage and mixing system according to the invention of FIG. 8, FIG. 10 shows a schematic cross-sectional view of the cartridge bottom of the storage and mixing system according to the invention of FIG. 8, and FIG. 11 shows a schematic perspective cross-sectional view of the cartridge bottom of the storage and mixing system according to the invention of FIG. 8.

A method according to the invention is described based on FIGS. 8 to 11, wherein the method according to the invention can also be readily applied to the embodiments according to FIGS. 1 to 7. The dispensing device, which is described based on FIGS. 8 to 11, can also be readily used in the embodiments of FIGS. 1 to 7, 12 and 13. The cartridge head 7 can be separated, or the plugs 9 can be removed from the passages in the cartridge head 7, and instead of the union nut 8, the dispensing tube 28 is screwed onto the cartridge 1. In this position, the dispensing device can be connected to the connector 10 or the fastening means 12 of the storage and mixing system. This is shown in FIG. 8.

FIGS. 8 to 11 show only a connector 42 for the connection to the fastening means 12 of the storage and mixing system, a pusher 44, and a mount 46 for the pusher 44 of the dispensing device. These parts and the remaining components of the dispensing device correspond to those of customary manually or electrically or pneumatically driven dispensing devices. The dispensing device includes a compartment for accommodating the storage and mixing system, wherein the storage and mixing system is held in a stable manner by the dispensing device at least on the front side in the region of the thread 14 and on the back side at the connector 10. The connector 42 is connected to the fastening means 12. The pusher 44, which acts as a push rod 44, can be moved or driven against the connector 42 of the dispensing device in the direction through the connector 42, or in the direction into the cartridge 1, since it is movably mounted in the mount 46 along the longitudinal axis thereof. The tip of the pusher 44 presses on the abutment surface 23 of the bending device 18. As a result, the bending device 18 and the two dispensing plungers 5, 6 are advanced in the direction of the dispensing tube 28.

The bending device 18 is advanced by the application of pressure onto the abutment surface 23 in the direction of the cartridge head 7 or the dispensing tube 28. The detent means 26 release from the depressions 38, and the dispensing plungers 5, 6 are pushed forward in the cavities 3, 4. The two cement components are pressed forward into the dispensing tube 28 in this process, where they are mixed. Upon further advancement of the bending device 18, not only are the dispensing plungers 5, 6 advanced further in the cavities 3, 4 of the cartridge 1, but the partition 2 is also displaced in the axial direction through the bending device 18 and is deflected and deformed in the bending device 18 and is detached from the inside wall of the cartridge 1 behind the dispensing plungers 5, 6. This situation is shown in FIG. 9, which illustrates that the pusher 44 of the dispensing device has driven the bending device 18 and the dispensing plungers 5, 6 forward. The partition 2 is fastened via the hole 20 to the mushroom-shaped pin 19 on the cartridge 1. This prevents the partition 2 from simply deforming in the region of the cavities 3, 4 and moving with the dispensing plungers 5, 6.

The partition 2 is guided through the gap of the passage in the bending device 18 to a deflection surface 50 inclined with respect to the axis of the cartridge 1 or to the deflection wall 22. Upon further advancement of the bending device 18, the deflection surface 50 or the deflection wall 22 presses the partition 2 in the direction of the inside wall of the cartridge 1. In the meantime, the cement components are pressed further out of the cavities 3, 4 and into the dispensing tube 28, where they are mixed. Finally, the fully mixed cement dough exits the dispensing tube 28 through the dispensing opening 32 and can be applied at the desired location. Depressions 37, which engage in detents (not shown) in the interior of the dispensing plungers 5, 6, are provided as mating detents 37 in the two cylinder segment-shaped legs of the bending device 18, which are inserted into the intended cavities in the dispensing plungers 5, 6 so as to connect these to the bending device 18 and thus to one another.

As a result of the design according to the invention, it is possible, despite the high viscosity of the pasty cement components, despite the flow resistance caused by the static mixer 30, and despite the force expenditure or energy expenditure required to deform the partition 2, that the resistance to the movement of the pusher 44 is not so great that the cartridge 1 cannot be pressed out using conventional, manually driven dispensing devices.

As is apparent from FIG. 12, the plugs 9 include a catch 58 in the form of protrusions, which engage in the cartridge head 7 over the edge of the passages in the direction of the inner chamber of the cartridge 1 and thereby latchingly engage with the cartridge head 7. As a result of the catch 58, it is achieved that the plugs 9 are not undesirably released from the cartridge head 7.

The bending device 18 roughly has the shape of a yoke and has a mirror plane as the plane of symmetry, wherein the axis of the storage and mixing system is located in the mirror plane. The side of the bending device 18 facing the cartridge head 7 is composed of two cylinder segments, which are cut in a plane parallel to the cylinder axis thereof, wherein two depressions 37 are provided on the lateral surface of the cylinder segments as mating detents 37 for a respective detent means in the dispensing plungers 5, 6. The two cylinder segments of the bending device 18 thus latchingly engage with the dispensing plungers 5, 6 when they are inserted into the intended openings on the back side of the dispensing plungers 5, 6 situated opposite the cartridge head 7.

The two cylinder segments are connected to one another by a circular plate. A gap, which is provided for the insertion of the partition 2, which is to say is aligned with the partition 2 when assembled, is present in the plate. The two walls 40 and the inclined deflection wall 22 comprising the deflection surface 50 on the inner side of the deflection wall 22 extend on the plate. The plate, the walls 40 and the deflection wall 22 bound the opening 21 and the passage, through which the partition 2, having detached or severed from the inside wall of the cartridge 1, moves while the bending device 18 is being moved forward in the direction of the dispensing tube 28. Blades (not shown), which sever the partition 2 in the region of the inside wall of the cartridge 1, can be located on both sides of the gap. However, it is preferred according to the invention if no blades are present on the bending device 18, since blades would make the design unnecessarily more costly.

A central perpendicular cylinder having a circular base surface 23, which forms the abutment surface 23 for the pusher 44 of the dispensing device, is located in the center on the back side of the plate. The two cylinder segments are held at a fixed distance from one another by the plate and the sleeve walls 19. The distance is selected such that the two dispensing plungers 5, 6, when these are placed on the cylinder segments of the bending device 18, are held a distance from one another which is slightly smaller than or no more than the same size as the thickness of the partition 2, which is to say 1 mm, for example. The bending device 18 should be made of a material that is hard enough to be able to deform the partition 2 when the bending device 18 is being advanced in the cartridge 1 in the direction of the cartridge head 7.

In all variants, the cartridge 1 and the connector 10 are preferably designed in one piece with one another and are preferably made of plastic material. With the exception of the seals 24, all parts of the storage and mixing systems can be made of plastic material by way of injection molding. The seals 24 are preferably made of rubber. The plate 7 for the cartridge head 7 can also be made of rubber or a rubber-elastic material. Preferred cement components are pasty starting components of a PMMA bone cement. However, theoretically, it is also possible to store and mix other cements, such as dental cements, two-component adhesives or other two-component systems that are mixed from pasty starting components, using a storage and mixing system according to the invention.

Figure 13:
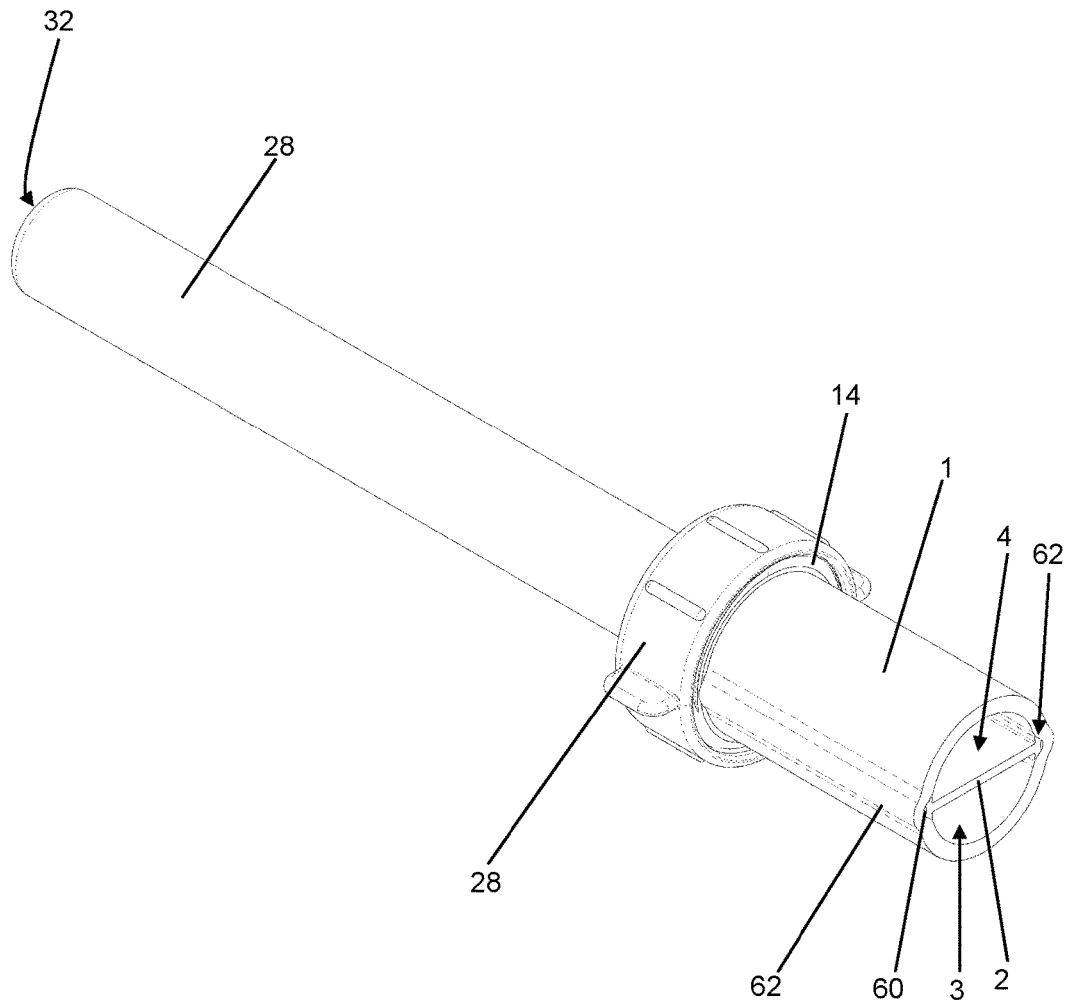
FIG. 13 shows a schematic perspective view of the front portion of an alternative storage and mixing system according to the invention, which is connected to a dispensing tube.

FIG. 13 shows a schematic perspective cross-sectional view of the front portion of a further alternative storage and mixing system according to the invention, which is connected to a dispensing tube 28. Again, the partition 2 divides the inner chamber of the cartridge 1 into two cavities 3, 4, which are separated from one another in a fluid-tight manner. The partition 2 is not connected in one piece to the inside wall of the cartridge 1. A seal 60, which seals the connection of the partition 2 to the inside wall of the cartridge 1, is provided on the partition 2 on the lateral edge on which the partition 2 is seated against the inside wall of the cartridge 1. The cartridge 1 of the storage and mixing system includes two longitudinal grooves 62 in the inner chamber, which extend in the inner chamber parallel to the axis of the cartridge 1 and in which the seals 60 of the partition 2 are seated. In FIG. 13, the back sides of the longitudinal grooves 62 are apparent as elevations and are referred to as a longitudinal groove 62 on one side (on the left in FIG. 13). As a result of the longitudinal grooves 62 and the seals 60, sufficient tightness of the cavities 3, 4 for long-term storage of the cement components is achieved. The composition of this storage and mixing system otherwise corresponds to the above-described storage and mixing devices. The movement of the bending device 18 causes the partition 2, together with the seal 60 thereon, to be lifted off the inside wall of the cartridge 1. The seal 60 can alternatively also be connected to the groove 62.

The characteristics of the invention disclosed in the above description, as well as in the claims, figures and exemplary embodiments may be essential for the implementation of the invention in its various embodiments either alone or in any arbitrary combination with each other.

LIST OF REFERENCE NUMERALS 1 cartridge
2 partition
3 cavity
4 cavity
5 dispensing plunger
6 dispensing plunger 7 cartridge head
8 union nut
9 plug
10 connector
12 fastening element
14 external thread
16 internal thread
18 bending device
19 pin/mushroom
20 hole
21 opening
22 inclined deflection wall
23 abutment surface
24 seal
26 detent means
28 dispensing tube
30 static mixer
32 dispensing opening
34 internal thread
36 seal
37 mating detent/depression
38 mating detent means/depression
40 wall
42 connector
44 pusher/push rod
46 mount
50 inclined deflection surface
58 catch
60 seal
62 axial groove (back side)

We claim:

1. A storage and mixing system for pasty two-component polymethyl methacrylate bone cements, the system comprising: a tubular cartridge having a cylindrical inner chamber; a cartridge head, that closes one end of the tubular cartridge on the front side; a partition disposed axially in the cylindrical inner chamber of the cartridge, wherein the partition divides the cylindrical inner chamber of the cartridge bounded by the cartridge head into two cavities spatially separated from one another, wherein a first pasty cement component is present in the first cavity and a second pasty cement component is present in the separate second cavity; two dispensing plungers disposed axially displaceably in the two cavities of the cartridge, wherein the dispensing plungers close the two cavities on the back side of the cavities situated opposite the cartridge head; a bending device for deforming the partition that is axially movable in the cartridge and is disposed or to be disposed behind the dispensing plungers, as seen from the cartridge head, wherein the bending device comprises a deflection surface that is inclined with respect to the axis of the cartridge and that presses the partition laterally in the direction of the inside wall of the cartridge if the bending device is pushed into the cartridge, wherein a rear end of the partition, that is disposed behind the dispensing plungers, as seen from the cartridge head, is fixable or is fastened to the cartridge so that the rear end of the partition does not detach from the cartridge if the bending device moves into the cartridge.

2. The storage and mixing system according to claim 1, wherein a fastening element is disposed at the rear end of the partition, wherein the fastening element is to be fastened to a mating fastening element in the region of the rear side of the cartridge, wherein a hole is provided in the partition as the fastening element, and a hook or a pin is provided as the mating fastening element.

3. The storage and mixing system according to claim 1, wherein a passage is provided in the bending device, or the bending device forms a passage together with the inside wall of the cartridge, wherein the deflection surface is provided in the passage, and the partition is to be fed through the passage or is fed through the passage, wherein the partition moves through the passage if the bending device moves into the cartridge.

4. The storage and mixing system according to claim 1, wherein the partition is connected to the inside wall of the cartridge via a predetermined breaking point, or the partition is detachably connected to the inside wall of the cartridge, such that the partition detaches from the inside wall of the cartridge if the partition is being deformed by the movement of the bending device into the cartridge.

5. The storage and mixing system according to claim 4, wherein the partition is detachably connected on both lateral edges to a respective guide element in or on the inside wall of the cartridge, and is inserted into a respective groove in the inside wall of the cartridge, wherein the guide element and the lateral edges of the partition are sealed in a fluid-tight manner with one another.

6. The storage and mixing system according to claim 1, wherein the dispensing plungers are connected or connectable to one another at the back side situated opposite the cartridge head via the bending device, and that the dispensing plungers are disposed at a distance from one another via the bending device such that the gap present between the dispensing plungers is smaller than or equal to the thickness of the partition.

7. The storage and mixing system according to claim 1, wherein the cavities have a semi-circular or circular segment-shaped cross-section, and the dispensing plungers have a matching cross-section, wherein the dispensing plungers close off the cavities in every axial position in the cavities.

8. The storage and mixing system according to claim 1, wherein the partition has a thickness of no more than 1.5 mm and/or that the partition has such a thickness that the partition can be deformed by the bending device, onto which an advancing force of 1 kN acts, and pushed in the direction of the inside wall of the cartridge.

9. The storage and mixing system according to claim 1, wherein the storage and mixing system comprises a dispensing tube, on which a fastening means for fastening the dispensing tube to the cartridge is provided, wherein the dispensing tube instead of the cartridge head is to be fastened to the cartridge.

10. The storage and mixing system according to claim 1, wherein the diameter of the inner chamber of the cartridge is smaller than or equal to 25 mm.

11. The storage and mixing system according to claim 1, wherein two passages are provided in the cartridge head, which connect the two cavities to the surrounding area of the storage and mixing system, wherein a removable plug is disposed in each of the passages.

12. The storage and mixing system according to claim 1, wherein the cartridge, the cartridge head, the partition, the bending device and the dispensing plungers are made of plastic material, wherein plastic materials are polyethylene co-vinyl alcohol, polybutylene terephthalate, polyethylene terephthalate, and polymethylmethacrylate-co-acrylonitrile.

13. The storage and mixing system according to claim 1, wherein the cartridge head is implemented by a rubber-elastic plate, that is fastened to the cartridge by way of a safety cap, wherein the safety cap blocks a movement of the rubber-elastic plate away from the cartridge with the aid of a protruding edge, and wherein the rubber-elastic plate, on the side facing the dispensing plungers, has a recess for accommodating the longitudinal side of the partition, and wherein two regions are defined by this accommodation in the rubber-elastic plate, wherein a passage, that is closed by a plug, is provided in each region.

14. The storage and mixing system according to claims, wherein the inclined deflection surface is surrounded by a wall of the bending device in some regions, such that the partition extending through the bending device is bent about the longitudinal axis of the partition by the wall of the bending device surrounding the inclined deflection surface.

15. The storage and mixing system according to claim 1, wherein the bending device is designed as an open hollow body, wherein an opening on the back side of the hollow body facing away from the dispensing plungers follows the inner contour of the cartridge in an arc-shaped manner, wherein the length of the arc is greater than or equal to the width of the partition.

16. The storage and mixing system according to claim 15, an extension of the partition on the back side of the partition situated opposite the cartridge head exits through the rear opening, and the partition is fixed at this end to at least one point of the cartridge.

17. The storage and mixing system according to claim 1, the partition is designed as a panel, that comprises at least one peripheral rubber-elastic seal on the narrow side.

18. A method for mixing pasty cement components of a pasty polymethyl methacrylate bone cement, utilizing storage and mixing system according to claim 1, the method consecutively comprising:
 a) removing the cartridge head from the cartridge, or removing at least two plugs from at least two passages in the cartridge head, wherein the cartridge is opened;
 b) placing on and connecting a dispensing tube to the opened cartridge, wherein the dispensing tube comprises a mixer;
 c) inserting the cartridge into a manually operable dispensing device, the dispensing device comprising an axially advanceable pusher for advancing the dispensing plungers in the cavities of the cartridge; and
 d) pressing out the pasty cement components with the aid of the dispensing device by axially advancing the dispensing plungers by way of the pusher,
 wherein the cement components are pushed into the dispensing tube, wherein the two cement components are mixed by the mixer in the dispensing tube to yield the pasty cement dough, and the mixed cement dough flows out of a dispensing opening of the dispensing tube,
 wherein, synchronously with the movement of the dispensing plungers, the bending device is pushed over the partition into the cartridge, and the partition is pushed by a deflection surface of the bending device in the direction of the inside wall of the cartridge at least so far in the direction of the inside wall of the cartridge that a further movement of the pusher of the dispensing device is not prevented by the partition or is not impaired by the partition.

19. The method according to claim 18, wherein the partition is bent in the axial direction by the bending device moving in the direction of the cartridge head, and that, as a result of the bending of the partition, the partition is detached from the inside wall of the cartridge, and is dislodged from the guide elements.

20. The method according to claim 18, wherein a fixation element fixes the partition to the back side of the cartridge such that an axial movement of the partition in the guide elements in front of the dispensing plungers is prevented.

21. The method according to claim 18, wherein the pusher of the dispensing device pushes onto the side of the bending device facing away from the dispensing plungers, and the dispensing plungers are driven by way of the bending device.

22. The method according to claim 18, wherein the side of the bending device facing away from the dispensing plungers comprises an abutment surface for placing thereon the front side of the pusher or of a plate attached thereto, that has the same size as or is larger than the cross-section of the pusher or than the support surface of the plate, wherein the cross-section of the pusher or the support surface of the plate is completely covered by the abutment surface when the pusher is being advanced, or the abutment surface protrudes beyond the cross-section of the pusher or the support surface of the plate, when the pusher is being advanced.

23. The method according to claim 18, wherein the dispensing device is manually drivable, or is drivable by compressed air or electrically.

24. A storage and mixing system for pasty two-component polymethyl methacrylate bone cements, the system comprising: a tubular cartridge having a cylindrical inner chamber; a cartridge head, that closes one end of the tubular cartridge on the front side; a partition disposed axially in the cylindrical inner chamber of the cartridge, wherein the partition divides the cylindrical inner chamber of the cartridge bounded by the cartridge head into two cavities spatially separated from one another, wherein a first pasty cement component is present in the first cavity and a second pasty cement component is present in the separate second cavity; two dispensing plungers disposed axially displaceably in the two cavities of the cartridge, wherein the dispensing plungers close the two cavities on the back side of the cavities situated opposite the cartridge head; a bending device for deforming the partition that is axially movable in the cartridge and is disposed or to be disposed behind the dispensing plungers, as seen from the cartridge head, wherein the bending device comprises a deflection surface that is inclined with respect to the axis of the cartridge and that presses the partition laterally in the direction of the inside wall of the cartridge if the bending device is pushed into the cartridge, wherein the bending device is designed as an open hollow body, wherein an opening on the back side of the hollow body facing away from the dispensing plungers follows the inner contour of the cartridge in an arc-shaped manner, wherein the length of the arc is greater than or equal to the width of the partition, and an extension of the partition on the back side of the partition situated opposite the cartridge head exits through the rear opening, and the partition is fixed at this end to at least one point of the cartridge.

* * * * *